US012589279B2

(12) United States Patent
Mason et al.

(10) Patent No.: US 12,589,279 B2
(45) Date of Patent: Mar. 31, 2026

(54) SYSTEMS AND METHODS OF USING ARTIFICIAL INTELLIGENCE AND MACHINE LEARNING FOR GENERATING AN ALIGNMENT PLAN CAPABLE OF ENABLING THE ALIGNING OF A USER'S BODY DURING A TREATMENT SESSION

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Brookfield, CT (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 735 days.

(21) Appl. No.: 17/834,515

(22) Filed: Jun. 7, 2022

(65) Prior Publication Data

US 2022/0339501 A1 Oct. 27, 2022

Related U.S. Application Data

(63) Continuation-in-part of application No. 17/739,906, filed on May 9, 2022, which is a continuation of
(Continued)

(51) Int. Cl.
*A63B 24/00* (2006.01)
*A63B 21/005* (2006.01)
(Continued)

(52) U.S. Cl.
CPC ...... *A63B 24/0075* (2013.01); *A63B 21/0058* (2013.01); *A63B 24/0062* (2013.01);
(Continued)

(58) Field of Classification Search
CPC ............ A63B 21/0058; A63B 24/0062; A63B 22/0605; A63B 2022/0094;
(Continued)

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
(Continued)

*Primary Examiner* — Vincent H Tran
(74) *Attorney, Agent, or Firm* — Dickinson Wright PLLC; Jonathan H. Harder; Stephen A. Mason

(57) ABSTRACT

Methods, systems, and computer-readable mediums for generating, by an artificial intelligence engine, an alignment plan capable of enabling, during a treatment session, the aligning of a user's body. The method comprises generating machine learning models trained to identify alignment plans. The method also comprises receiving treatment data that comprises a first position of the user's body, aspects of a treatment plan, and one or more attributes of the user. The
(Continued)

method further comprises generating the alignment plan by using the machine learning models. The generating is based on at least the aspects of the treatment plan and at least one of the one or more attributes of the user. The alignment plan may comprise a target position of the user's body and one or more elements for adjusting the user's body from the first position to the target position. The method also comprises transmitting the plan to a computing device.

20 Claims, 13 Drawing Sheets

Related U.S. Application Data application No. 17/150,938, filed on Jan. 15, 2021, now Pat. No. 11,325,005, which is a continuation-in-part of application No. 17/021,895, filed on Sep. 15, 2020, now Pat. No. 11,071,597.

(60) Provisional application No. 63/208,158, filed on Jun. 8, 2021, provisional application No. 62/910,232, filed on Oct. 3, 2019.

(51) Int. Cl.

| | |
|---|---|
| *G06N 20/00* | (2019.01) |
| *G16H 10/60* | (2018.01) |
| *G16H 20/30* | (2018.01) |
| *A63B 22/00* | (2006.01) |
| *A63B 22/06* | (2006.01) |

(52) U.S. Cl.
CPC ............. *G06N 20/00* (2019.01); *G16H 10/60* (2018.01); *G16H 20/30* (2018.01); *A63B 2022/0094* (2013.01); *A63B 22/0605* (2013.01); *A63B 2024/0093* (2013.01)

(58) Field of Classification Search
CPC ........ A63B 2024/0093; A63B 24/9975; G16H 20/60; G16H 20/30; G06N 20/00
See application file for complete search history.

(56) References Cited

U.S. PATENT DOCUMENTS

| | | | |
|---|---|---|---|
| 4,822,032 | A | 4/1989 | Whitmore et al. |
| 4,860,763 | A | 8/1989 | Schminke |
| 4,869,497 | A | 9/1989 | Stewart et al. |
| 4,932,650 | A | 6/1990 | Bingham et al. |
| 5,137,501 | A | 8/1992 | Mertesdorf |
| 5,161,430 | A | 11/1992 | Febey |
| 5,202,794 | A | 4/1993 | Schnee et al. |
| 5,240,417 | A | 8/1993 | Smithson et al. |
| 5,247,853 | A | 9/1993 | Dalebout |
| 5,256,117 | A | 10/1993 | Potts et al. |
| D342,299 | S | 12/1993 | Birrell et al. |
| 5,282,748 | A | 2/1994 | Little |
| 5,284,131 | A | 2/1994 | Gray |
| 5,316,532 | A | 5/1994 | Butler |
| 5,318,487 | A | 6/1994 | Golen |
| 5,324,241 | A | 6/1994 | Artigues et al. |
| 5,336,147 | A | 8/1994 | Sweeney, III |
| 5,338,272 | A | 8/1994 | Sweeney, III |
| 5,356,356 | A | 10/1994 | Hildebrandt |
| 5,361,649 | A | 11/1994 | Slocum, Jr. |
| D359,777 | S | 6/1995 | Hildebrandt |
| 5,429,140 | A | 7/1995 | Burdea et al. |
| 5,458,022 | A | 10/1995 | Mattfeld et al. |
| 5,487,713 | A | 1/1996 | Butler |
| 5,566,589 | A | 10/1996 | Buck |
| 5,580,338 | A | 12/1996 | Scelta et al. |
| 5,676,349 | A | 10/1997 | Wilson |
| 5,685,804 | A | 11/1997 | Whan-Tong et al. |

| | | | |
|---|---|---|---|
| 5,738,636 | A | 4/1998 | Saringer et al. |
| 5,860,941 | A | 1/1999 | Saringer et al. |
| 5,950,813 | A | 9/1999 | Hoskins et al. |
| 6,007,459 | A | 12/1999 | Burgess |
| D421,075 | S | 2/2000 | Hildebrandt |
| 6,053,847 | A | 4/2000 | Stearns et al. |
| 6,077,201 | A | 6/2000 | Cheng |
| 6,102,834 | A | 8/2000 | Chen |
| 6,110,130 | A | 8/2000 | Kramer |
| 6,155,958 | A | 12/2000 | Goldberg |
| 6,162,189 | A | 12/2000 | Girone et al. |
| 6,182,029 | B1 | 1/2001 | Friedman |
| D438,580 | S | 3/2001 | Shaw |
| 6,253,638 | B1 | 7/2001 | Bermudez |
| 6,267,735 | B1 | 7/2001 | Blanchard et al. |
| 6,273,863 | B1 | 8/2001 | Avni et al. |
| D450,100 | S | 11/2001 | Hsu |
| D450,101 | S | 11/2001 | Hsu |
| D451,972 | S | 12/2001 | Easley |
| D452,285 | S | 12/2001 | Easley |
| D454,605 | S | 3/2002 | Lee |
| 6,371,891 | B1 | 4/2002 | Speas |
| D459,776 | S | 7/2002 | Lee |
| 6,413,190 | B1 | 7/2002 | Wood et al. |
| 6,430,436 | B1 | 8/2002 | Richter |
| 6,436,058 | B1 | 8/2002 | Krahner et al. |
| 6,450,923 | B1 | 9/2002 | Vatti |
| 6,474,193 | B1 | 11/2002 | Farney |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,543,309 | B2 | 4/2003 | Heim |
| 6,589,139 | B1 | 7/2003 | Butterworth |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,640,662 | B1 | 11/2003 | Baxter |
| 6,652,425 | B1 | 11/2003 | Martin et al. |
| 6,659,946 | B1 | 12/2003 | Batchelor et al. |
| 6,820,517 | B1 | 11/2004 | Farney |
| 6,865,969 | B2 | 3/2005 | Stevens |
| 6,890,312 | B1 | 5/2005 | Priester et al. |
| 6,895,834 | B1 | 5/2005 | Baatz |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,204,788 | B2 | 4/2007 | Andrews |
| 7,209,886 | B2 | 4/2007 | Kimmel |
| 7,226,394 | B2 | 6/2007 | Johnson |
| RE39,904 | E | 10/2007 | Lee |
| 7,406,003 | B2 | 7/2008 | Burkhardt et al. |
| 7,507,188 | B2 | 3/2009 | Nurre |
| 7,594,879 | B2 | 9/2009 | Johnson |
| 7,628,730 | B1 | 12/2009 | Watterson et al. |
| D610,635 | S | 2/2010 | Hildebrandt |
| 7,778,851 | B2 | 8/2010 | Schoenberg et al. |
| 7,809,601 | B2 | 10/2010 | Shaya et al. |
| 7,815,551 | B2 | 10/2010 | Merli |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,988,599 | B2 | 8/2011 | Ainsworth et al. |
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell |
| 8,113,991 | B2 | 2/2012 | Kutliroff |
| 8,172,724 | B2 | 5/2012 | Solomon |
| 8,177,732 | B2 | 5/2012 | Einav et al. |
| 8,287,434 | B2 | 10/2012 | Zavadsky et al. |
| 8,298,123 | B2 | 10/2012 | Hickman |

(56) References Cited

U.S. PATENT DOCUMENTS

| | | | |
|---|---|---|---|
| 8,371,990 B2 | 2/2013 | Shea |
| 8,419,593 B2 | 4/2013 | Ainsworth et al. |
| 8,465,398 B2 | 6/2013 | Lee et al. |
| 8,503,086 B2 | 8/2013 | French |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,615,529 B2 | 12/2013 | Reiner |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Brenda |
| 9,256,711 B2 | 2/2016 | Horseman |
| 9,272,091 B2 | 3/2016 | Skelton |
| 9,272,185 B2 | 3/2016 | Dugan |
| 9,283,434 B1 | 3/2016 | Wu |
| 9,295,878 B2 | 3/2016 | Corbalis et al. |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,773,330 B1 | 9/2017 | Douglas |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,974,478 B1 | 5/2018 | Brokaw |
| 9,977,587 B2 | 5/2018 | Mountain |
| 9,993,181 B2 | 6/2018 | Ross |
| 9,997,082 B2 | 6/2018 | Kaleal |
| 10,004,946 B2 | 6/2018 | Ross |
| 10,026,052 B2 | 7/2018 | Brown et al. |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,322,315 B2 | 6/2019 | Foley et al. |
| 10,325,070 B2 | 6/2019 | Beale et al. |
| 10,327,697 B1 | 6/2019 | Stein et al. |
| 10,362,940 B2 | 7/2019 | Tran |
| 10,369,021 B2 | 8/2019 | Zoss et al. |
| 10,380,866 B1 | 8/2019 | Ross et al. |
| 10,413,222 B1 | 9/2019 | Kayyall |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,741,285 B2 | 8/2020 | Moturu |
| 10,777,200 B2 | 9/2020 | Will et al. |
| D899,605 S | 10/2020 | Ross et al. |
| 10,792,495 B2 | 10/2020 | Izvorski et al. |
| 10,814,170 B2 | 10/2020 | Wang et al. |
| 10,857,426 B1 | 12/2020 | Neumann |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,902,944 B1 | 1/2021 | Casey |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,094,400 B2 | 8/2021 | Riley et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| 11,185,738 B1 | 11/2021 | McKirdy et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |

(56) References Cited

U.S. PATENT DOCUMENTS

| | | |
|---|---|---|
| 11,229,788 B1 | 1/2022 | John |
| 11,265,234 B2 | 3/2022 | Guaneri et al. |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,347,829 B1 | 5/2022 | Sclar et al. |
| 11,348,683 B2 | 5/2022 | Guaneri et al. |
| 11,370,328 B2 * | 6/2022 | Main .................... B60N 2/16 |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,437,137 B1 | 9/2022 | Harris |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,553,969 B1 | 1/2023 | Lang et al. |
| 11,621,067 B1 | 4/2023 | Nolan |
| 11,636,944 B2 | 4/2023 | Hanrahan et al. |
| 11,654,327 B2 | 5/2023 | Phillips et al. |
| 11,663,673 B2 | 5/2023 | Pyles |
| 11,673,024 B2 | 6/2023 | Omid-Zohoor |
| 11,701,548 B2 | 7/2023 | Posnack et al. |
| 11,776,676 B2 * | 10/2023 | Savolainen ............ G16H 20/30 |
| | | 482/4 |
| 11,944,579 B2 | 4/2024 | Sankai |
| 11,957,960 B2 | 4/2024 | Bissonnette et al. |
| 12,004,871 B1 | 6/2024 | Fazeli |
| 12,020,511 B1 | 6/2024 | Denton et al. |
| 12,057,210 B2 | 8/2024 | Akinola et al. |
| 12,205,704 B2 | 1/2025 | Hosoi et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 | 6/2005 | Tashiro |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1 | 6/2006 | Choi et al. |
| 2006/0199700 A1 | 9/2006 | LaStayo et al. |
| 2006/0247095 A1 | 11/2006 | Rummerfield |
| 2006/0277074 A1 | 12/2006 | Einav |
| 2007/0042868 A1 | 2/2007 | Fisher et al. |
| 2007/0118389 A1 | 5/2007 | Shipon |
| 2007/0118406 A1 | 5/2007 | Killin et al. |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2008/0312040 A1 | 12/2008 | Ochi |
| 2009/0011907 A1 | 1/2009 | Radow et al. |
| 2009/0037334 A1 | 2/2009 | Hsu |
| 2009/0058635 A1 | 3/2009 | LaLonde et al. |
| 2009/0070138 A1 | 3/2009 | Langheier et al. |
| 2009/0157617 A1 | 6/2009 | Herlocker |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0062818 A1 | 3/2010 | Haughay, Jr. |
| 2010/0076348 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0293003 A1 | 11/2010 | Abbo |
| 2010/0298102 A1 | 11/2010 | Bosecker et al. |
| 2010/0326207 A1 | 12/2010 | Topel |
| 2010/0332583 A1 | 12/2010 | Szabo |
| 2011/0010188 A1 | 1/2011 | Yoshikawa et al. |
| 2011/0047108 A1 | 2/2011 | Chakrabarty et al. |
| 2011/0082007 A1 | 4/2011 | Birrell |
| 2011/0087137 A1 | 4/2011 | Hanoun |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218462 A1 | 9/2011 | Smith |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0167709 A1 | 7/2012 | Chen et al. |
| 2012/0183939 A1 | 7/2012 | Aragones et al. |

(56) References Cited

U.S. PATENT DOCUMENTS

| | | |
|---|---|---|
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0066647 A1 | 3/2013 | Andrie |
| 2013/0079925 A1 | 3/2013 | Alaklabi et al. |
| 2013/0083054 A1 | 4/2013 | Bayouk |
| 2013/0108594 A1 | 5/2013 | Martin-Rendon et al. |
| 2013/0110545 A1 | 5/2013 | Smallwood |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0158368 A1 | 6/2013 | Pacione |
| 2013/0165195 A1 | 6/2013 | Watterson |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0038781 A1 | 2/2014 | Foley et al. |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0108035 A1 | 4/2014 | Akbay |
| 2014/0113261 A1 | 4/2014 | Akiba |
| 2014/0113768 A1 | 4/2014 | Lin et al. |
| 2014/0135173 A1 | 5/2014 | Watterson |
| 2014/0149129 A1 | 5/2014 | Getchius |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0200414 A1 | 7/2014 | Osorio |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0275816 A1 | 9/2014 | Sandmore |
| 2014/0303540 A1 | 10/2014 | Baym |
| 2014/0309083 A1 | 10/2014 | Dugan |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0046192 A1 | 2/2015 | Raduchel |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Campana Aguilera et al. |
| 2015/0149217 A1 | 5/2015 | Kaburagi |
| 2015/0151162 A1 | 6/2015 | Dugan |
| 2015/0157938 A1 | 6/2015 | Domansky et al. |
| 2015/0161331 A1 | 6/2015 | Oleynik |
| 2015/0161876 A1 | 6/2015 | Castillo |
| 2015/0174446 A1 | 6/2015 | Chiang |
| 2015/0196804 A1* | 7/2015 | Koduri ............... G06Q 10/0639 |
| | | 482/8 |
| 2015/0196805 A1 | 7/2015 | Koduri |
| 2015/0199494 A1* | 7/2015 | Koduri ................... G16H 20/30 |
| | | 700/91 |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0331997 A1 | 11/2015 | Joao |
| 2015/0335950 A1* | 11/2015 | Eder ................. A63B 22/0605 |
| | | 482/8 |
| 2015/0335951 A1* | 11/2015 | Eder ...................... G16H 20/30 |
| | | 482/8 |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta |
| 2016/0015995 A1 | 1/2016 | Leung et al. |
| 2016/0023081 A1 | 1/2016 | Popa-Simil et al. |
| 2016/0045170 A1 | 2/2016 | Migita |
| 2016/0081594 A1 | 3/2016 | Gaddipati |
| 2016/0086500 A1* | 3/2016 | Kaleal, III ............... G09B 5/06 |
| | | 434/257 |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0250519 A1 | 9/2016 | Watterson |
| 2016/0275259 A1 | 9/2016 | Nolan et al. |
| 2016/0287166 A1 | 10/2016 | Tran |
| 2016/0294837 A1 | 10/2016 | Turgeman |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361025 A1 | 12/2016 | Reicher et al. |
| 2016/0361597 A1 | 12/2016 | Cole et al. |
| 2016/0373477 A1 | 12/2016 | Moyle |
| 2017/0000422 A1 | 1/2017 | Moturu et al. |
| 2017/0004260 A1 | 1/2017 | Moturu et al. |
| 2017/0011179 A1 | 1/2017 | Arshad et al. |
| 2017/0017760 A1 | 1/2017 | Freese et al. |
| 2017/0032092 A1 | 2/2017 | Mink et al. |
| 2017/0033375 A1 | 2/2017 | Ohmori et al. |
| 2017/0042467 A1 | 2/2017 | Herr et al. |
| 2017/0043160 A1 | 2/2017 | Goodall et al. |
| 2017/0046488 A1 | 2/2017 | Pereira |
| 2017/0065851 A1 | 3/2017 | Deluca et al. |
| 2017/0069223 A1 | 3/2017 | Cramer et al. |
| 2017/0080320 A1 | 3/2017 | Smith |

(56) References Cited

U.S. PATENT DOCUMENTS

| | | |
|---|---|---|
| 2017/0091422 A1 | 3/2017 | Kumar et al. |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0136298 A1 | 5/2017 | Bae |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0169177 A1 | 6/2017 | Beale |
| 2017/0173391 A1 | 6/2017 | Wiebe |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0228517 A1 | 8/2017 | Saliman et al. |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0258370 A1 | 9/2017 | Plotnik-Peleg et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0277841 A1 | 9/2017 | Shankar et al. |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0291067 A1 | 10/2017 | Jang et al. |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0352157 A1 | 12/2017 | Madabhushi |
| 2017/0360586 A1 | 12/2017 | Dempers et al. |
| 2017/0361165 A1 | 12/2017 | Miller et al. |
| 2017/0367606 A1* | 12/2017 | Lee ..................... A61H 1/001 |
| 2017/0368413 A1 | 12/2017 | Shavit |
| 2018/0017806 A1 | 1/2018 | Wang et al. |
| 2018/0036591 A1 | 2/2018 | King et al. |
| 2018/0036593 A1 | 2/2018 | Ridgel et al. |
| 2018/0052962 A1 | 2/2018 | Van Der Koijk et al. |
| 2018/0052968 A1 | 2/2018 | Hickle et al. |
| 2018/0056104 A1 | 3/2018 | Cromie et al. |
| 2018/0056130 A1 | 3/2018 | Bitran et al. |
| 2018/0060494 A1 | 3/2018 | Dias et al. |
| 2018/0070864 A1* | 3/2018 | Schuster ............... G16H 40/63 |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078149 A1 | 3/2018 | Fonte et al. |
| 2018/0078182 A1 | 3/2018 | Chen |
| 2018/0078843 A1 | 3/2018 | Tran et al. |
| 2018/0085615 A1 | 3/2018 | Astolfi et al. |
| 2018/0089385 A1 | 3/2018 | Gupta |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0103859 A1 | 4/2018 | Provenzano |
| 2018/0113985 A1 | 4/2018 | Gandy et al. |
| 2018/0116741 A1 | 5/2018 | Garcia Kilroy et al. |
| 2018/0117417 A1 | 5/2018 | Davis |
| 2018/0130555 A1 | 5/2018 | Chronis et al. |
| 2018/0133551 A1 | 5/2018 | Chang |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0232492 A1 | 8/2018 | Al-Alul et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0255110 A1 | 9/2018 | Dowlatkhah et al. |
| 2018/0256079 A1 | 9/2018 | Yang et al. |
| 2018/0256939 A1 | 9/2018 | Malcolm |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0285463 A1 | 10/2018 | Choi et al. |
| 2018/0290017 A1 | 10/2018 | Fung |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0353812 A1 | 12/2018 | Lannon et al. |
| 2018/0360340 A1 | 12/2018 | Rehse et al. |
| 2018/0361203 A1 | 12/2018 | Wang |
| 2018/0366225 A1 | 12/2018 | Mansi et al. |
| 2018/0373844 A1 | 12/2018 | Ferrandez-Escamez et al. |
| 2019/0005195 A1 | 1/2019 | Peterson |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0108912 A1 | 4/2019 | Spurlock, III |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0118066 A1 | 4/2019 | Cardona |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0143193 A1 | 5/2019 | Kim |
| 2019/0145774 A1 | 5/2019 | Ellis |
| 2019/0163876 A1 | 5/2019 | Remme et al. |
| 2019/0167988 A1 | 6/2019 | Shahriari et al. |

(56)　　　　　　References Cited

U.S. PATENT DOCUMENTS

| | | |
|---|---|---|
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0247718 A1 | 8/2019 | Blevins |
| 2019/0251456 A1 | 8/2019 | Constantin |
| 2019/0251723 A1 | 8/2019 | Coppersmith |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0283247 A1* | 9/2019 | Chang ................. A61B 5/1121 |
| 2019/0290191 A1 | 9/2019 | Leppäluoto et al. |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0371472 A1 | 12/2019 | Blanchard |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0015736 A1 | 1/2020 | Alhathal |
| 2020/0034665 A1 | 1/2020 | Ghanta |
| 2020/0034707 A1 | 1/2020 | Kivatinos et al. |
| 2020/0038703 A1 | 2/2020 | Cleary et al. |
| 2020/0051446 A1* | 2/2020 | Rubinstein ............. G06N 20/00 |
| 2020/0054922 A1 | 2/2020 | Azaria |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0098463 A1 | 3/2020 | Arunachalam et al. |
| 2020/0121987 A1 | 4/2020 | Loh |
| 2020/0129808 A1 | 4/2020 | Fomin |
| 2020/0139194 A1 | 5/2020 | Min |
| 2020/0143922 A1 | 5/2020 | Chekroud et al. |
| 2020/0151595 A1* | 5/2020 | Jayalath ............. A63B 21/0442 |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1* | 6/2020 | Kapure .................. A61H 3/008 |
| 2020/0176098 A1 | 6/2020 | Lucas et al. |
| 2020/0188774 A1* | 6/2020 | Fung .................... A63F 13/235 |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0261763 A1 | 8/2020 | Park |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0320454 A1 | 10/2020 | Almashor |
| 2020/0334972 A1 | 10/2020 | Gopalakrishnan |
| 2020/0338394 A1 | 10/2020 | Neumann |
| 2020/0346072 A1 | 11/2020 | Shah |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0391080 A1* | 12/2020 | Powers .................. G16H 50/50 |
| 2020/0395112 A1 | 12/2020 | Ronner |
| 2020/0398083 A1 | 12/2020 | Adelsheim |
| 2020/0401224 A1 | 12/2020 | Cotton |
| 2020/0402638 A1* | 12/2020 | Song .................... A61B 5/0022 |
| 2020/0402662 A1 | 12/2020 | Esmailian et al. |
| 2020/0410374 A1 | 12/2020 | White |
| 2020/0410385 A1 | 12/2020 | Otsuki |
| 2020/0410893 A1 | 12/2020 | Ridington |
| 2020/0411162 A1 | 12/2020 | Lien et al. |
| 2020/0411170 A1 | 12/2020 | Brown |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0015560 A1 | 1/2021 | Boddington et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng |
| 2021/0098099 A1 | 4/2021 | Neumann |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134427 A1 | 5/2021 | Mason et al. |
| 2021/0134428 A1 | 5/2021 | Mason |
| 2021/0134429 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0202090 A1 | 7/2021 | ODonovan et al. |
| 2021/0202103 A1 | 7/2021 | Bostic et al. |
| 2021/0205660 A1* | 7/2021 | Shavit .................... A63B 21/16 |
| 2021/0217516 A1 | 7/2021 | Nash |
| 2021/0236020 A1 | 8/2021 | Matijevich et al. |
| 2021/0240853 A1 | 8/2021 | Carlson |
| 2021/0241137 A1 | 8/2021 | Jain et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |

(56) References Cited

U.S. PATENT DOCUMENTS

| | | | |
|---|---|---|---|
| 2021/0350914 A1 | 11/2021 | Guaneri et al. | |
| 2021/0350926 A1 | 11/2021 | Mason et al. | |
| 2021/0354002 A1 | 11/2021 | Schaefer | |
| 2021/0361514 A1 | 11/2021 | Choi et al. | |
| 2021/0366587 A1 | 11/2021 | Mason et al. | |
| 2021/0375425 A1* | 12/2021 | Zhang | G06V 40/23 |
| 2021/0383909 A1 | 12/2021 | Mason et al. | |
| 2021/0391091 A1 | 12/2021 | Mason | |
| 2021/0394011 A1* | 12/2021 | Neuhaus | A63B 71/0622 |
| 2021/0398668 A1 | 12/2021 | Chock et al. | |
| 2021/0406738 A1* | 12/2021 | O'Donncha | G16H 20/30 |
| 2021/0407670 A1 | 12/2021 | Mason et al. | |
| 2021/0407681 A1 | 12/2021 | Mason et al. | |
| 2022/0000556 A1 | 1/2022 | Casey et al. | |
| 2022/0015838 A1 | 1/2022 | Posnack | |
| 2022/0016480 A1 | 1/2022 | Bissonnette et al. | |
| 2022/0016482 A1 | 1/2022 | Bissonnette | |
| 2022/0016484 A1 | 1/2022 | Bissonnett et al. | |
| 2022/0016485 A1 | 1/2022 | Bissonnette | |
| 2022/0016486 A1 | 1/2022 | Bissonnette et al. | |
| 2022/0020469 A1 | 1/2022 | Tanner | |
| 2022/0044806 A1 | 2/2022 | Sanders et al. | |
| 2022/0047921 A1 | 2/2022 | Bissonnette | |
| 2022/0066548 A1* | 3/2022 | Helot | B60K 35/654 |
| 2022/0079690 A1 | 3/2022 | Mason et al. | |
| 2022/0080256 A1 | 3/2022 | Arn et al. | |
| 2022/0080265 A1 | 3/2022 | Watterson | |
| 2022/0096006 A1 | 3/2022 | Wu et al. | |
| 2022/0105384 A1 | 4/2022 | Hacking et al. | |
| 2022/0105385 A1 | 4/2022 | Hacking et al. | |
| 2022/0105390 A1 | 4/2022 | Yuasa | |
| 2022/0115133 A1 | 4/2022 | Mason et al. | |
| 2022/0117514 A1 | 4/2022 | Kuhn et al. | |
| 2022/0118218 A1 | 4/2022 | Bense et al. | |
| 2022/0122724 A1 | 4/2022 | Durlach et al. | |
| 2022/0126169 A1 | 4/2022 | Mason | |
| 2022/0133576 A1 | 5/2022 | Choi et al. | |
| 2022/0148725 A1 | 5/2022 | Mason et al. | |
| 2022/0158916 A1 | 5/2022 | Mason et al. | |
| 2022/0165398 A1 | 5/2022 | Avila-Hernandez et al. | |
| 2022/0176039 A1 | 6/2022 | Lintereur et al. | |
| 2022/0181004 A1 | 6/2022 | Zilca et al. | |
| 2022/0193491 A1* | 6/2022 | Mason | A63B 21/00178 |
| 2022/0230729 A1 | 7/2022 | Mason | |
| 2022/0238222 A1 | 7/2022 | Neuberg | |
| 2022/0238223 A1 | 7/2022 | Mason | |
| 2022/0258935 A1 | 8/2022 | Kraft | |
| 2022/0262483 A1 | 8/2022 | Rosenberg et al. | |
| 2022/0262504 A1 | 8/2022 | Bratty et al. | |
| 2022/0266094 A1 | 8/2022 | Mason et al. | |
| 2022/0270738 A1 | 8/2022 | Mason et al. | |
| 2022/0273985 A1 | 9/2022 | Jeong et al. | |
| 2022/0273986 A1 | 9/2022 | Mason | |
| 2022/0288460 A1 | 9/2022 | Mason | |
| 2022/0288461 A1 | 9/2022 | Ashley et al. | |
| 2022/0288462 A1 | 9/2022 | Ashley et al. | |
| 2022/0293257 A1 | 9/2022 | Guaneri et al. | |
| 2022/0300787 A1 | 9/2022 | Wall et al. | |
| 2022/0304881 A1 | 9/2022 | Choi et al. | |
| 2022/0304882 A1 | 9/2022 | Choi | |
| 2022/0305291 A1 | 9/2022 | Hibbard | |
| 2022/0305328 A1 | 9/2022 | Choi et al. | |
| 2022/0314072 A1 | 10/2022 | Bissonnette et al. | |
| 2022/0314075 A1 | 10/2022 | Mason et al. | |
| 2022/0323826 A1 | 10/2022 | Khurana | |
| 2022/0327714 A1 | 10/2022 | Cook et al. | |
| 2022/0327807 A1 | 10/2022 | Cook et al. | |
| 2022/0328181 A1 | 10/2022 | Mason et al. | |
| 2022/0330823 A1 | 10/2022 | Janssen | |
| 2022/0331663 A1 | 10/2022 | Mason | |
| 2022/0336077 A1 | 10/2022 | Chen et al. | |
| 2022/0338761 A1 | 10/2022 | Maddahi et al. | |
| 2022/0339052 A1 | 10/2022 | Kim | |
| 2022/0339501 A1 | 10/2022 | Mason et al. | |
| 2022/0342969 A1 | 10/2022 | Watterson et al. | |
| 2022/0346703 A1 | 11/2022 | Abdo et al. | |
| 2022/0370851 A1 | 11/2022 | Guidarelli et al. | |
| 2022/0384010 A1* | 12/2022 | Kanayama | G16H 20/30 |
| 2022/0384012 A1 | 12/2022 | Mason | |
| 2022/0392591 A1 | 12/2022 | Guaneri et al. | |
| 2022/0395232 A1 | 12/2022 | Locke | |
| 2022/0401783 A1 | 12/2022 | Choi | |
| 2022/0415469 A1 | 12/2022 | Mason | |
| 2022/0415471 A1 | 12/2022 | Mason | |
| 2023/0001268 A1 | 1/2023 | Bissonnette et al. | |
| 2023/0013530 A1 | 1/2023 | Mason | |
| 2023/0014598 A1 | 1/2023 | Mason et al. | |
| 2023/0029639 A1 | 2/2023 | Roy | |
| 2023/0047253 A1 | 2/2023 | Gnanasambandam et al. | |
| 2023/0048040 A1 | 2/2023 | Hacking et al. | |
| 2023/0051751 A1 | 2/2023 | Hacking et al. | |
| 2023/0055078 A1 | 2/2023 | Malcolm | |
| 2023/0058605 A1 | 2/2023 | Mason | |
| 2023/0060039 A1 | 2/2023 | Mason | |
| 2023/0072368 A1 | 3/2023 | Mason | |
| 2023/0078793 A1 | 3/2023 | Mason | |
| 2023/0119461 A1 | 4/2023 | Mason | |
| 2023/0190100 A1 | 6/2023 | Stump | |
| 2023/0197240 A1 | 6/2023 | Rosenberg | |
| 2023/0201656 A1 | 6/2023 | Hacking et al. | |
| 2023/0207097 A1 | 6/2023 | Mason | |
| 2023/0207124 A1 | 6/2023 | Walsh et al. | |
| 2023/0215539 A1 | 7/2023 | Rosenberg et al. | |
| 2023/0215552 A1 | 7/2023 | Khotilovich et al. | |
| 2023/0218950 A1 | 7/2023 | Belson et al. | |
| 2023/0245747 A1 | 8/2023 | Rosenberg et al. | |
| 2023/0245748 A1 | 8/2023 | Rosenberg et al. | |
| 2023/0245750 A1 | 8/2023 | Rosenberg et al. | |
| 2023/0245751 A1 | 8/2023 | Rosenberg et al. | |
| 2023/0249599 A1* | 8/2023 | Nicola | B60N 2/0248 297/284.6 |
| 2023/0253089 A1 | 8/2023 | Rosenberg et al. | |
| 2023/0255555 A1 | 8/2023 | Sundaram et al. | |
| 2023/0263428 A1 | 8/2023 | Hull et al. | |
| 2023/0274813 A1 | 8/2023 | Rosenberg et al. | |
| 2023/0282329 A1 | 9/2023 | Mason et al. | |
| 2023/0364471 A1 | 11/2023 | Choi et al. | |
| 2023/0364472 A1 | 11/2023 | Posnack | |
| 2023/0368886 A1 | 11/2023 | Rosenberg | |
| 2023/0377710 A1 | 11/2023 | Chen et al. | |
| 2023/0377711 A1 | 11/2023 | Rosenberg | |
| 2023/0377712 A1 | 11/2023 | Rosenberg | |
| 2023/0386639 A1 | 11/2023 | Rosenberg | |
| 2023/0390627 A1 | 12/2023 | Bolton | |
| 2023/0395231 A1 | 12/2023 | Rosenberg | |
| 2023/0395232 A1 | 12/2023 | Rosenberg | |
| 2024/0029856 A1 | 1/2024 | Rosenberg | |
| 2024/0058651 A1 | 2/2024 | Bissonnette | |
| 2024/0177846 A1 | 5/2024 | Gnanasambandam | |
| 2024/0203580 A1 | 6/2024 | Mason | |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105263448 A | 1/2016 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |

(56) References Cited

FOREIGN PATENT DOCUMENTS

| | | | |
|---|---|---|---|
| CN | 106510985 | A | 3/2017 |
| CN | 106621195 | A | 5/2017 |
| CN | 107066819 | A | 8/2017 |
| CN | 107430641 | A | 12/2017 |
| CN | 107551475 | A | 1/2018 |
| CN | 107736982 | A | 2/2018 |
| CN | 107930021 | A | 4/2018 |
| CN | 108078737 | A | 5/2018 |
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |

(56) References Cited

FOREIGN PATENT DOCUMENTS

| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 A1 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 A1 | 5/2003 |
| WO | 2005018453 A1 | 3/2005 |
| WO | 2005074369 A2 | 8/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2008140780 A1 | 11/2008 |
| WO | 2009003170 A1 | 12/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016151364 A1 | 9/2016 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018027080 A1 | 2/2018 |
| WO | 2018081795 A1 | 5/2018 |
| WO | 2018171853 A1 | 9/2018 |
| WO | 2019022706 A1 | 1/2019 |
| WO | 2019106003 A1 | 6/2019 |
| WO | 2019143940 A1 | 7/2019 |
| WO | 2020014710 A2 | 1/2020 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021061061 A1 | 4/2021 |
| WO | 2021090267 A1 | 5/2021 |
| WO | 2021138620 A1 | 7/2021 |
| WO | 2021216881 A1 | 10/2021 |
| WO | 2021236961 A1 | 11/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024013267 A1 | 1/2024 |
| WO | 2024107807 A1 | 5/2024 |

OTHER PUBLICATIONS

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Davenport et al., "The Potential For Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

(56)                 References Cited

OTHER PUBLICATIONS

Yin Chieh et al., "A Virtual Reality-Cycling Training System for Lower Limb Balance Improvement", BioMed Research International, vol. 2016, pp. 1-10.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-·Q+ and ePARmed-·X+ Validation of the PAR-·Q+ and ePARmed-·X+," Health & Fitness Journal of Canada, 2011, 9 pages, vol. 4, No. 2.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Gerbild et al., "Physical Activity to Improve Erectile Dysfunction: A Systematic Review of Intervention Studies," Sexual Medicine, 2018, 15 pages.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform For Personalized Predictive Analytics", ProQuest LLC, Jul. 2017, 185 pages.

Jeong et al., "Remotely controlled biking is associated with improved adherence to prescribed cycling speed," Technology and Health Care 23, 2015, 7 pages.

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "Curate.AI: Optimizing Personalized Medicine with Artificial Intelligence, "Slas Technology: Translating Life Sciences Innovation, 2020, 11 pages.

Amiya et al., "Is Exercise Training Appropriate for Patients With Advanced Heart Failure Receiving Continuous Inotropic Infusion? A Review," 2018, pp. 1-9, vol. 12, Japan.

Chu Hin Yee, "Physical Activity, Sedentary Behaviour and Health: From Measurements to Recommendations," 2018, 255 pages.

Ahmed et al., "Artificial Intelligence With Multi-Functional Machine Learning Platform Development For Better Healthcare And Precision Medicine," Database (Oxford), 2020, pp. 1-35, vol. 2020.

Davenport et al., "The Potential For Artificial Intelligence in Healthcare," Future Healthcare Journal, 2019, pp. 94-98, vol. 6, No. 2.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities For Artificial Intelligence To Transform How Care Is Delivered," Nov. 2019, American Hospital Association, pp. 1-12.

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

(56) References Cited

OTHER PUBLICATIONS

International Searching Authority, Search Report and Written Opinion for International Application No. PCT/US2020/021876, Date of Mailing May 28, 2020, 8 pages.

International Searching Authority, Search Report and Written Opinion for International Application No. PCT/US2020/051008, Date of Mailing Dec. 10, 2020, 9 pages.

International Searching Authority, Search Report and Written Opinion for International Application No. PCT/US2020/056661, Date of Mailing Feb. 12, 2021, 12 pages.

International Searching Authority, Search Report and Written Opinion for International Application No. PCT/US2021/032807, Date of Mailing Sep. 6, 2021, 11 pages.

Matrix, R3xm Recumbent Cycle, retrieved on Aug. 4, 2020, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

Jeong et al., "Computer-assisted upper extremity training using interactive biking exercise (iBikE) platform," Sep. 2012, pp. 1-5, 34th Annual International Conference of the IEEE EMBS.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

"Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec. 2017) (Year: 2017)".

Fuller, Carole G.; Diagnosis and treatment considerations with comorbid developmentally disabled populations; Journal of Clinical Psychology 54.1: 1-10. John Wiley and Sons Inc. (Jan. 1998) (Year: 1998).

He, Jianxing et al. The practical implementation of artificial intelligence technologies in medicine. Nature Medicine; New York vol. 25, Iss. 1. Jan. 2019. (Year: 2019).

CG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC2013.2262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.

Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.

Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.

Karboub et al, "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.

Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.

International Preliminary Report on Patentability of International Application No. PCT/2024/022550, Date of Mailing Sep. 20, 2025, 7 pages.

Joudaki et. al., "Using Data Mining to Detect Health Care Fraud and Abuse: A Review of Literature", Global Journal of Health Science, vol. 7, No. 1, 2015 (Year: 2015).

* cited by examiner

302

108

Steps Today
1355

304

Knee Angle
72°

Force
12.5lbs

202

Session Time
0:04:13

Force
27lbs

202

200

Pain Level
3

104

114

102

702

122

Move the chair toward the cycling machine

AT A PROCESSING DEVICE

900

902 ~ GENERATE ONE OR MORE MACHINE LEARNING MODELS TRAINED TO IDENTIFY ALIGNMENT PLANS

904 ~ RECEIVE TREATMENT DATA INCLUDING FIRST POSITION OF USER'S BODY, ASPECTS OF TREATMENT PLAN FOR USER, AND ONE OR MORE ATTRIBUTES OF USER

906 ~ GENERATE ALIGNMENT PLAN USING ONE OR MORE MACHINE LEARNING MODELS

908 ~ TRANSMIT ALIGNMENT PLAN TO COMPUTING DEVICE

1100

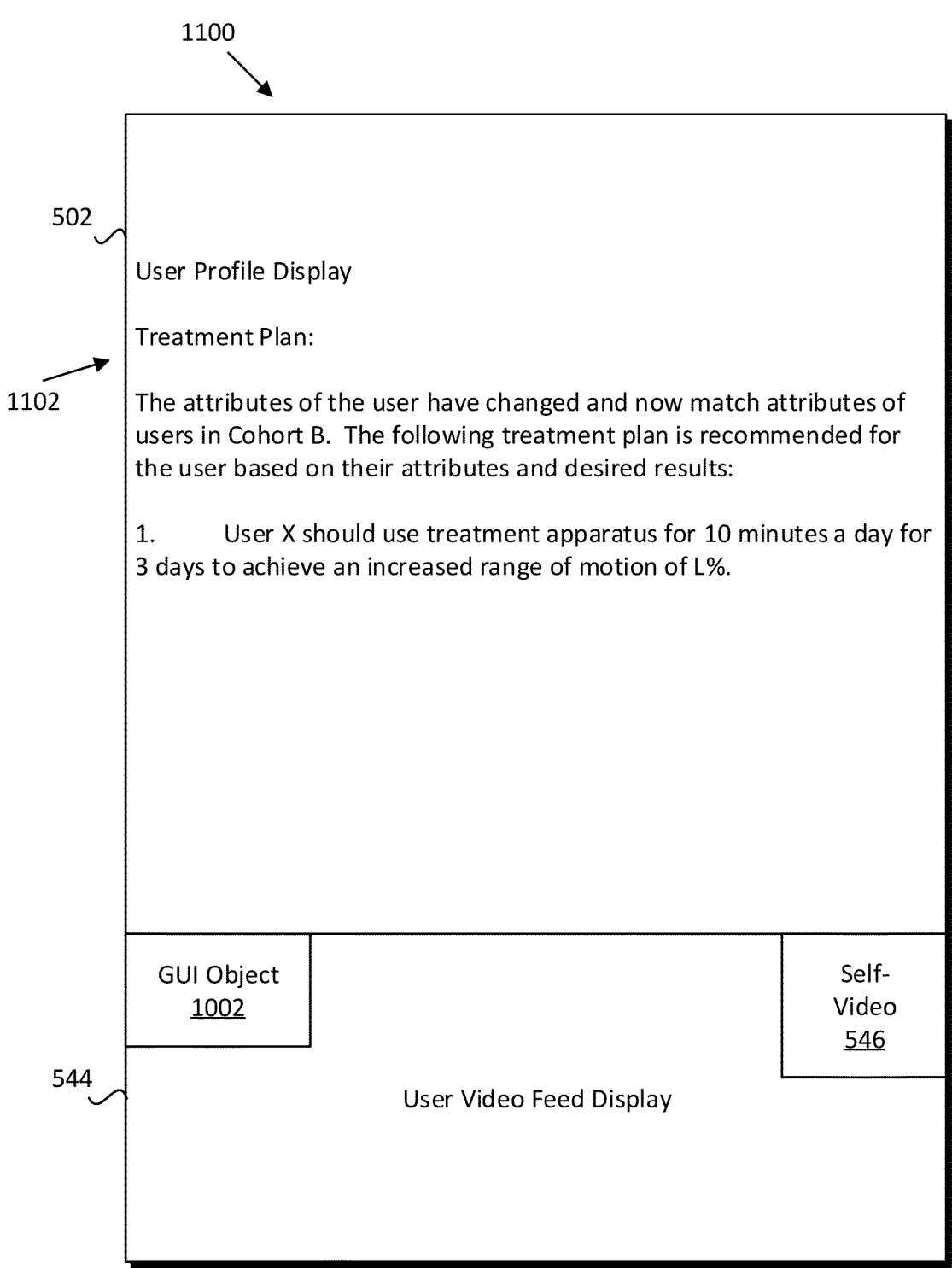

502

1102

User Profile Display

Treatment Plan:

The attributes of the user have changed and now match attributes of users in Cohort B. The following treatment plan is recommended for the user based on their attributes and desired results:

1.     User X should use treatment apparatus for 10 minutes a day for 3 days to achieve an increased range of motion of L%.

GUI Object
1002

Self-Video
546

544

User Video Feed Display

FIG. 11

SYSTEMS AND METHODS OF USING ARTIFICIAL INTELLIGENCE AND MACHINE LEARNING FOR GENERATING AN ALIGNMENT PLAN CAPABLE OF ENABLING THE ALIGNING OF A USER'S BODY DURING A TREATMENT SESSION

CROSS-REFERENCE TO OTHER APPLICATIONS

This application is a continuation-in-part of U.S. patent application Ser. No. 17/739,906 filed May 9, 2022, titled "Systems and Methods for Using Machine Learning to Control an Electromechanical Device Used for Prehabilitation, Rehabilitation, and/or Exercise", which is a continuation of U.S. patent application Ser. No. 17/150,938, filed Jan. 15, 2021, titled "Systems and Methods for Using Machine Learning to Control an Electromechanical Device Used for Prehabilitation, Rehabilitation, and/or Exercise" (now U.S. Pat. No. 11,325,005), which is a continuation-in-part of U.S. patent application Ser. No. 17/021,895, filed Sep. 15, 2020, titled "Telemedicine for Orthopedic Treatment" (now U.S. Pat. No. 11,071,597), which claims priority to and the benefit of U.S. Provisional Patent Application Ser. No. 62/910,232, filed Oct. 3, 2019, titled "Telemedicine for Orthopedic Treatment", the entire disclosures of which are hereby incorporated by reference for all purposes.

This application also claims priority to and the benefit of U.S. Provisional Patent Application Ser. No. 63/208,158, filed Jun. 8, 2021, titled "Systems and Methods of Using Artificial Intelligence and Machine Learning for Generating an Alignment Plan Capable of Enabling the Aligning of a User's Body During a Treatment Session", the entire disclosure of which is hereby incorporated by reference for all purposes.

BACKGROUND

Various treatment apparatuses may be used by people for exercising and/or rehabilitating parts of their bodies. For example, to maintain a desired level of fitness, people may operate treatment apparatuses for a period of time or distance as part of a workout regime. In another example, a person may undergo knee surgery and a physician may provide a treatment plan for prehabilitation that includes operating an exercise bike for a period of time and/or distance periodically to strengthen and/or improve flexibility of the knee.

Properly aligning a user's body can improve the outcome of a treatment session. For example, if a treatment plan is applied to the user's knee, it may be desirable for the user's knee to be bent or extended. It may be difficult, however, for the user to "self-position," i.e., to bend or extend the user's knee to a degree or angle or position without reference to a standard or goal-based position, inter alia, and any such difficulty may arise from several factors including, for example, pain or stress from moving the user's knee, limited user mobility, the user's lack of knowledge of the treatment plan, the user's lack of medical knowledge, or a combination thereof.

While at least some of these issues can be remedied by a healthcare professional attending to the user in a healthcare facility, it may be desirable and efficient to remotely perform the treatment plan for the user, i.e., outside the healthcare facility. For example, the treatment plan may be administered to the user at the user's home or in some location other than the healthcare facility. However, in these instances, direct assistance or consultation from a healthcare professional may not be available.

SUMMARY

Artificial intelligence and machine learning can be used for determining a target body alignment for a user that is tailored to, for example, attributes of the specific user, aspects of a specific treatment plan, attributes of a specific treatment apparatus (e.g., an exercise bike, a rowing machine, etc.), attributes of a specific user support apparatus (e.g., a chair, a weight bench, etc.), or a combination thereof. Artificial intelligence and machine learning can also be used for generating an alignment plan capable of enabling the user to move their body to the target body alignment with a limited number of steps and in a manner than avoids causing the physical discomfort for the user. Accordingly, the present disclosure provides methods, systems, and non-transitory computer-readable media for, among other things, generating, by an artificial intelligence engine, an alignment plan capable of enabling, during a treatment session, the aligning of a user's body.

The present disclosure provides a method for generating, by an artificial intelligence engine, an alignment plan capable of enabling, during a treatment session, the aligning of a user's body. The method comprises generating, by the artificial intelligence engine, one or more machine learning models trained to identify alignment plans. The method also comprises receiving treatment data. The treatment data comprises a first position of the user's body, aspects of a treatment plan for the user, and one or more attributes of the user. The method further comprises generating, by the artificial intelligence engine that is configured to use the one or more machine learning models, the alignment plan. The generating is based on at least the aspects of the treatment plan and at least one of the one or more attributes of the user. The alignment plan comprises a target position of the user's body and one or more elements for adjusting the user's body from the first position to the target position. The method also comprises transmitting the alignment plan to a computing device.

The present disclosure also provides a system for generating, by an artificial intelligence engine, an alignment plan capable of enabling, during a treatment session, the aligning of a user's body. The system comprises, in one implementation, a memory device and a processing device. The memory device stores instructions. The processing device is communicatively coupled to the memory device. The processing device is configured to execute the instructions to generate, by the artificial intelligence engine, one or more machine learning models trained to identify alignment plans. The processing device is also configured to execute the instructions to receive treatment data. The treatment data comprises a first position of the user's body, aspects of a treatment plan for the user, and one or more attributes of the user. The processing device is further configured to execute the instructions to generate, by the artificial intelligence engine that is configured to use the one or more machine learning models, the alignment plan. The generating is based on at least the aspects of the treatment plan and at least one of the one or more attributes of the user. The alignment plan comprises a target position of the user's body and one or more elements for adjusting the user's body from the first position to the target position. The processing device is also configured to execute the instructions to transmit the alignment plan to a computing device.

The present disclosure further provides a tangible, non-transitory computer-readable medium storing instructions that, when executed, cause a processing device to generate, by an artificial intelligence engine, one or more machine learning models trained to identify alignment plans. The instructions also cause the processing device to receive treatment data. The treatment data comprises a first position of a user's body, aspects of a treatment plan for the user, and one or more attributes of the user. The instructions further cause the processing device to generate, by the artificial intelligence engine that is configured to user the one or more machine learning models, the alignment plan. The generating is based on at least the aspects of the treatment plan and at least one of the one or more attributes of the user. The alignment plan comprises a target position of the user's body and one or more elements for adjusting the user's body from the first position to the target position. The instructions also cause the processing device to transmit the alignment plan to a computing device.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description, taken in conjunction with the accompanying drawings. It is emphasized that, according to common practice, the various features of the drawings are not necessarily to-scale. On the contrary, the dimensions of the various features may be—and typically are—arbitrarily expanded or reduced for the purpose of clarity.

FIG. 11 is a diagram of an example of an overview display of a clinical portal presenting, in real-time during a telemedicine session, recommended treatment plans that, as a result of user data changing, have themselves changed, in accordance with some implementations of the present disclosure.

NOTATION AND NOMENCLATURE

Figure 1:
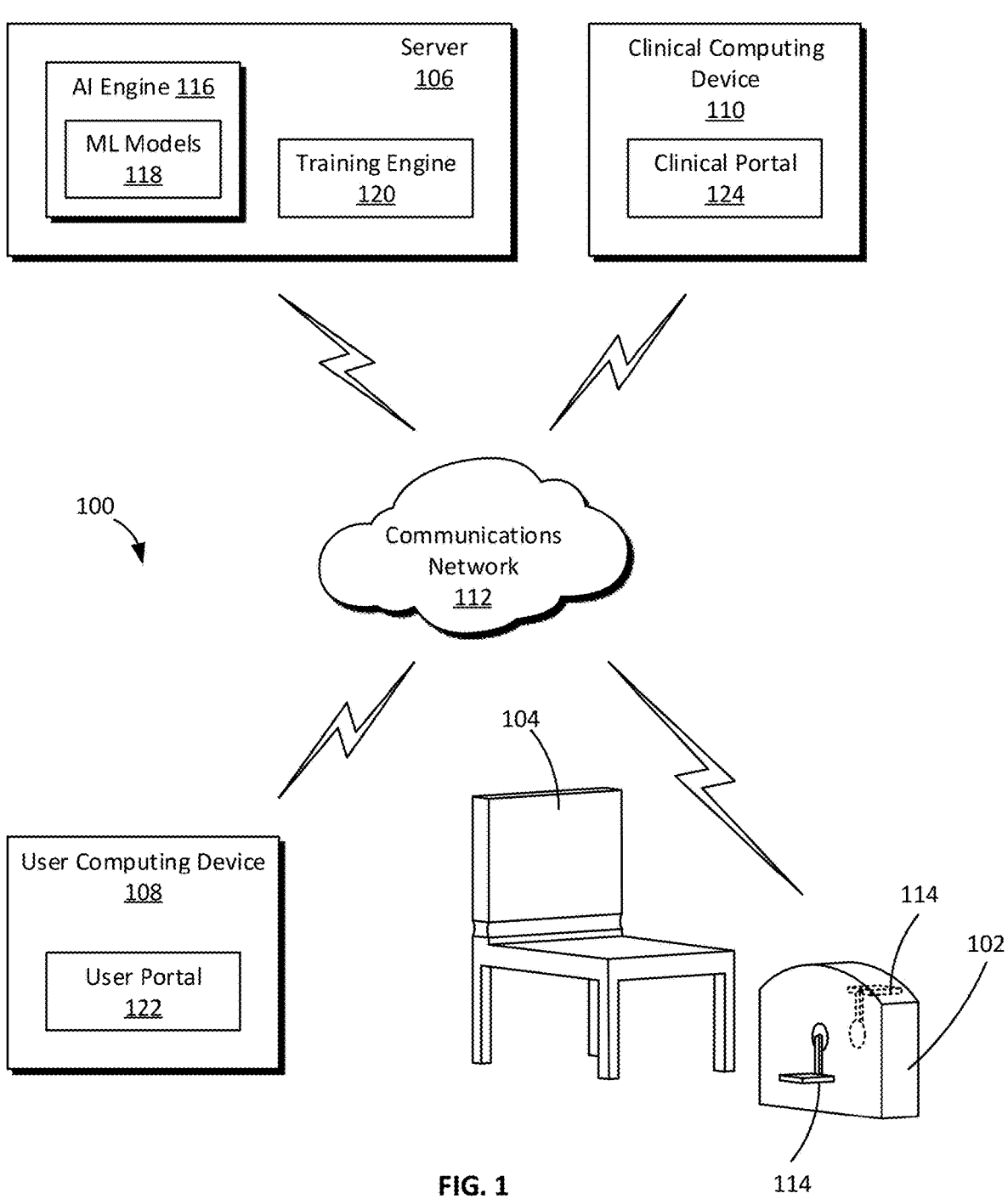
FIG. 1 is a block diagram of an example of a system for generating an alignment plan capable of enabling, during a treatment session, the aligning of a user's body, in accordance with some implementations of the present disclosure.

Various terms are used to refer to particular system components. A particular component may be referred to commercially or otherwise by different names. Further, a particular component (or the same or similar component) may be referred to commercially or otherwise by different names. Consistent with this, nothing in the present disclosure shall be deemed to distinguish between components that differ only in name but not in function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example implementations only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example implementations. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating a body part of a person. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on a person, a treatment protocol for the person using a treatment apparatus, a diet regimen, a medication regimen, a sleep regimen, additional regimens, or some combination thereof.

"Remote medical assistance," also referred to, inter alia, as remote medicine, telemedicine, telemed, teletherapeutic, telmed, tel-med, or telehealth, is an at least two-way communication between a healthcare professional or professionals, such as a physician or a physical therapist, and a patient (e.g., a user) using audio and/or audiovisual and/or other sensorial or perceptive (e.g., tactile, gustatory, haptic, pressure-sensing-based or electromagnetic (e.g., neurostimulative)) communications (e.g., via a computer, a smartphone, or a tablet).

A "healthcare professional" may refer to a doctor, physician assistant, nurse, chiropractor, dentist, physical therapist, acupuncturist, physical trainer, coach, personal trainer, neurologist, cardiologist, or the like. A "healthcare professional" may also refer to any person with a credential, license, degree, or the like in the field of medicine, physical therapy, rehabilitation, or the like.

"Real-time" may refer to less than or equal to 2 seconds. "Near real-time" may refer to any interaction of a sufficiently short time to enable two individuals to engage in a dialogue via such user interface, and will generally be less than 10 seconds (or any suitable proximate difference between two different times) but greater than 2 seconds.

"Results" may refer to medical results or medical outcomes. Results and outcomes may refer to responses to medical actions. A "medical action(s)" may refer to any suitable action(s) performed by a healthcare professional, and such action or actions may include diagnoses, prescriptions for treatment plans, prescriptions for treatment apparatuses, and the making, composing and/or executing of appointments, telemedicine sessions, prescription of medicines, telephone calls, emails, text messages, and the like.

DETAILED DESCRIPTION

The following discussion is directed to various implementations of the present disclosure. Although one or more of these implementations may be preferred, the implementations disclosed should not be interpreted, or otherwise used, as limiting the scope of the present disclosure, including the claims. In addition, one skilled in the art will understand that the following description has broad application, and the discussion of any implementation is meant only to be exemplary of that implementation, and not intended to intimate that the scope of the disclosure, including the claims, is limited to that implementation.

FIG. 1 is a block diagram of an example of a system 100 for generating alignment plans capable of enabling, during a treatment session, the aligning of a user's body, in accordance with some implementations of the present disclosure. The system 100 illustrated in FIG. 1 includes a treatment apparatus 102, a user support apparatus 104, a server 106, a user computing device 108, and a clinical computing device 110. The system 100 illustrated in FIG. 1 is provided as one example of such a system. The methods described herein may be used with systems having fewer, additional, or different components in different configurations than the system 100 illustrated in FIG. 1. For example, in some implementations, the system 100 may include fewer or additional computing devices, may include additional treatment apparatuses, may include additional user support apparatuses, and may include additional servers.

The various components of the system 100 may communicate with each other using suitable wireless and/or wired communication protocols over a communications network 112. The communications network 112 may be a wired network, a wireless network, or both. All or parts of the communications network 112 may be implemented using various networks, for example and without limitation, a cellular data network, the Internet, a Bluetooth™ network, a Near-Field Communications (NFC) network, a Z-Wave network, a ZigBee network, a wireless local area network (for example, Wi-Fi), a wireless accessory Personal Area Networks (PAN), cable, an Ethernet network, satellite, a machine-to-machine (M2M) autonomous network, and a public switched telephone network. In some implementations, communications with other external components (not shown) may occur over the communications network 112.

The treatment apparatus 102 is configured to be manipulated by the user and/or to manipulate one or more specific body parts of the user for performing activities according, for example, to a treatment plan. In some implementations, the treatment apparatus 102 may take the form of an exercise and rehabilitation apparatus configured to perform and/or to aid in the performance of a rehabilitation regimen, which may be an orthopedic rehabilitation regimen, and the treatment includes rehabilitation of a specific body part of the user, such as a joint or a bone or a muscle group. The treatment apparatus 102 may be any suitable medical, rehabilitative, therapeutic, etc. apparatus configured to be controlled distally via a computing device to treat a user and/or exercise the user. The treatment apparatus 102 may be an electromechanical machine including one or more weights, an electromechanical bicycle, an electromechanical spinwheel, a smart-mirror, a treadmill, a balance board, or the like. The treatment apparatus 102 may include, for example, pedals 114 on opposite sides. The treatment apparatus 102 may be operated by a user engaging the pedals 114 with their feet or their hands and rotating the pedals 114. The body part may include, for example, a spine, a hand, a foot, a knee, or a shoulder. The body part may include a part of a joint, a bone, or a muscle group, such as one or more vertebrae, a tendon, or a ligament. Examples of the treatment apparatus 102 are further described below in relation to FIGS. 2A and 2B.

The user support apparatus 104 is configured to support and/or align the user's body while performing activities, for example, according to a treatment plan. In some implementations, the user support device 104 may support and/or align multiple parts of the user's body. For example, the user support apparatus 104 is illustrated in FIG. 1 as an upright chair with a backrest. Alternatively or additionally, the user support apparatus 104 may comprise a different type of chair such as a stool, a Roman chair, and the like. The user support apparatus 104 may also comprise any other type of device on which a user sits or lies down, such as a bench (e.g., a weight bench), a bed, a yoga mat, a yoga wedge, straps, and the like. In some implementations, the user support device 104 may support and/or align a single part of the user's entire body. For example, the user support device 104 may comprise a foam roller, a yoga brick, and the like. In some implementations, the user support apparatus 104 may include one or more portions. For example, the user support apparatus 104 may include a backrest (or seatback) designed to support the user in a vertical, or substantially upright, position. Further, the backrest may be movable, or rotatable, thereby supporting the user in a horizontal, or substantially flat, position. Alternatively or additionally, the user support apparatus 104 may include armrests. The armrests may be movable, and accordingly, the user support apparatus 104 can move the user's arms and associated body parts of the arms. Alternatively or additionally, the user support apparatus 104 may include a footrest. The footrest may be movable, and accordingly, the user support apparatus 104 can move the user's feet and associated body parts of the feet. Moreover, the footrests may place the user's feet in a pronated or supinated position. In some implementations, the user support apparatus 104 may include other portions such as a seat rest, a harness, a balance board, or a combination thereof. In some implementations, one or more portions of the user support apparatus 104 may be designed to move (or actuate) in multiple directions, including, for example, along three different axes (e.g., x-, y-, and z-axes of a Cartesian coordinate system). Moreover, in some implementations, one or more movable portions of the user support apparatus 104 may be designed to rotate about at least one axis. The user support apparatus 104 may be configured in alternative arrangements and is not limited to the example implementations described and illustrated in the present disclosure.

The server 106 is configured to store and to provide data related to managing alignment and/or treatment plans. The server 106 may include one or more computers and may take the form of a distributed and/or virtualized computer or computers. The server 106 may be configured to store data regarding the alignment and/or treatment plans. For example, the server 106 may be configured to hold system data, such as data pertaining to treatment plans for treating one or more users. The server 106 may also be configured to store data regarding performance by a user in following a treatment plan. For example, the server 106 may be configured to hold user data, such as data pertaining to one or more users, including data representing each user's performance within the treatment plan. In addition, the server 106 may store attributes (e.g., personal, performance, measurement, etc.) of users, the alignment plans followed by users, and the results of the alignment plans may use correlations and other statistical or probabilistic measures to enable the partitioning of or to partition the alignment plans into different user cohort-equivalent databases. For example, the data for a first cohort of first users having a first similar injury, a first similar medical condition, a first similar medical procedure performed, a first alignment plan followed by the first user, and a first result of the alignment plan may be stored in a first user database. The data for a second cohort of second users having a second similar injury, a second similar medical condition, a second similar medical procedure performed, a second alignment plan followed by the second user, and a second result of the alignment plan may be stored in a second user database. Any single attribute or any combination of attributes may be used to separate the cohorts of users. In some implementations, the different cohorts of users may be stored in different partitions or volumes of the same database. There is no specific limit to the number of different cohorts of users allowed, other than as limited by mathematical combinatoric and/or partition theory.

This attribute data, alignment plan data, treatment plan data, and results data may be obtained from numerous treatment apparatuses and/or computing devices over time and stored, for example, in a database (not shown). The attribute data, alignment plan data, treatment plan data, and results data may be correlated in user-cohort databases. The attributes of the users may include personal information, performance information, measurement information, or a combination thereof.

In addition to historical information about other users stored in the user cohort-equivalent databases, real-time or near-real-time information based on the current user's attributes about a current user being treated may be stored in an appropriate user cohort-equivalent database. The attributes of the user may be determined to match or be similar to the attributes of another user in a particular cohort (e.g., cohort A) and the user may be assigned to that cohort.

In some implementations, the server 106 executes an artificial intelligence (AI) engine 116 that uses one or more machine learning models 118 to perform at least one of the implementations disclosed herein. The server 106 may include a training engine 120 capable of generating the one or more machine learning models 118. The training engine 120 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 120 may be cloud-based, a real-time software platform, or an embedded system (e.g., microcode-based and/or implemented) and it may include privacy software or protocols, and/or security software or protocols.

The user computing device 108 may be used by a user of the treatment apparatus 102 to obtain information about alignment plans and/or treatment plans. The user computing device 108 may also be used by the user to adjust settings on the treatment apparatus 102. The user computing device 108 may also be used by the user to provide feedback about alignment plans and/or treatment plans. The user computing device 108 may also be used by the user to communicate with a healthcare professional. The user computing device 108 illustrates in FIG. 1 includes a user portal 122. The user portal 122 is configured to communicate information to a user and to receive feedback from the user. The user portal 122 may include one or more input devices (e.g., a keyboard, a mouse, a touch-screen input, a gesture sensor, a microphone, a processor configured for voice recognition, a telephone, a trackpad, or a combination thereof). The user portal 122 may also include one of more output devices (e.g., a computer monitor, a display screen on a tablet, smartphone, or a smart watch). The one or more output devices may include other hardware and/or software components such as a projector, virtual reality capability, augmented reality capability, etc. The one or more output devices may incorporate various different visual, audio, or other presentation technologies. For example, at least one of the output devices may include a non-visual display, such as an audio signal, which may include spoken language and/or other sounds such as tones, chimes, and/or melodies, which may signal different conditions and/or directions. At least one of the output devices may include one or more different display screens presenting various data and/or interfaces or controls for use by the user. At least one of the output devices may include graphics, which may be presented by a web-based interface and/or by a computer program or application (App.).

The clinical computing device 110 may be used by a healthcare professional to remotely communicate with and monitor a user. The clinical computing device 110 may also be used by the healthcare professional to remotely monitor and adjust settings on the treatment apparatus 102. The clinical computing device 110 illustrates in FIG. 1 includes a clinical portal 124. The clinical portal 124 is configured to communicate information to a healthcare professional and to receive feedback from the healthcare professional. The clinical portal 124 may include one or more input devices such as any of the ones described above in relation to the user portal 122. The clinical portal 124 may also include one or more output devices such as any of the ones described above in relation to the user portal 122. The clinical portal 124 may be configured for use by a person having responsibility for the treatment plan, such as an orthopedic surgeon.

The clinical portal 124 may be used by a healthcare professional, to remotely communicate with the user portal 122 and/or the treatment apparatus 102. Such remote communications may enable the assistant to provide assistance or guidance to a user using the system 100. More specifically, the clinical portal 124 may be configured to communicate a telemedicine signal via, for example, the communications network 112. A telemedicine signal may comprises one of an audio signal, an audio-visual signal, an interface control signal for controlling a function of the user portal 122, an interface monitor signal for monitoring a status of the user portal 122, an apparatus control signal for changing an operating parameter of the treatment apparatus 102, and/or an apparatus monitor signal for monitoring a status of the treatment apparatus 102. In some implementations, each of the control signals may be unidirectional, conveying commands from the clinical portal 124 to the user portal 122. In some implementations, in response to successfully receiving a control signal and/or to communicate successful and/or unsuccessful implementation of the requested control action, an acknowledgement message may be sent from the user portal 122 to the clinical portal 124. In some implementations, each of the monitor signals may be unidirectional, status-information commands from the user portal 122 to the clinical portal 124. In some implementations, an acknowledgement message may be sent from the clinical portal 124 to the user portal 122 in response to successfully receiving one of the monitor signals.

In some implementations, the user portal 122 may be configured as a pass-through for the apparatus control signals and the apparatus monitor signals between the treatment apparatus 102 and one or more other devices, such as the clinical portal 124 and/or the server 106. For example, the user portal 122 may be configured to transmit an apparatus control signal in response to an apparatus control signal within the telemedicine signal from the clinical portal 124.

In some implementations, one or more portions of the telemedicine signal may be generated from a prerecorded source (e.g., an audio recording, a video recording, or an animation) for presentation by the user portal 122 of the user computing device 108. For example, a tutorial video may be streamed from the server 106 and presented upon the user portal 122. Content from the prerecorded source may be requested by the user via user portal 122. Alternatively, via a control on the clinical portal 124, the healthcare professional may cause content from the prerecorded source to be played on the user portal 122.

In some implementations, clinical portal 124 may be configured to provide voice-based functionalities, with hardware and/or software configured to interpret spoken instructions by the healthcare professional by using one or more microphones. The clinical portal 124 may include functionality provided by or similar to existing voice-based assistants such as Siri by Apple, Alexa by Amazon, Google Assistant, or Bixby by Samsung. The clinical portal 124 may include other hardware and/or software components. The clinical portal 124 may include one or more general purpose devices and/or special-purpose devices.

The clinical portal 124 may take one or more different forms including, for example, a computer monitor or display screen on a tablet, a smartphone, or a smart watch. The clinical portal 124 may include other hardware and/or software components such as projectors, virtual reality capabilities, or augmented reality capabilities, etc. The clinical portal 124 may incorporate various different visual, audio, or other presentation technologies. For example, the clinical portal 124 may include a non-visual display, such as an audio signal, which may include spoken language and/or other sounds such as tones, chimes, melodies, and/or compositions, which may signal different conditions and/or directions. The clinical portal 124 may comprise one or more different display screens presenting various data and/or interfaces or controls for use by the assistant. The clinical portal 124 may include graphics, which may be presented by a web-based interface and/or by a computer program or application (App.).

In some implementations, the system 100 may provide computer translation of language from the clinical portal 124 to the user portal 122 and/or vice-versa. The computer translation of language may include computer translation of spoken language and/or computer translation of text, wherein the text and/or spoken language may be any language, formal or informal, current or outdated, digital, quantum or analog, invented, human or animal (e.g., dolphin) or ancient, with respect to the foregoing, e.g., Old English, Zulu, French, Japanese, Klingon, Kobaïan, Attic Greek, Modern Greek, etc., and in any form, e.g., academic, dialectical, patois, informal, e.g., "electronic texting," etc. Additionally or alternatively, the system 100 may provide voice recognition and/or spoken pronunciation of text. For example, the system 100 may convert spoken words to printed text and/or the system 100 may audibly speak language from printed text. The system 100 may be configured to recognize spoken words by any or all of the user and the healthcare professional. In some implementations, the system 100 may be configured to recognize and react to spoken requests or commands by the user. For example, the system 100 may automatically initiate a telemedicine session in response to a verbal command by the user (which may be given in any one of several different languages).

In some implementations, the server 106 may generate aspects of the clinical portal 124 for presentation by the clinical portal 124. For example, the server 106 may include a web server configured to generate the display screens for presentation upon the clinical portal 124. For example, the artificial intelligence engine 116 may generate alignment plans and treatment plans for users and generate the display screens including those alignment plans and treatment plans for presentation on the clinical portal 124. In some implementations, the clinical portal 124 may be configured to present a virtualized desktop hosted by the server 106. In some implementations, the server 106 may be configured to communicate with the clinical portal 124 via the communications network 112. In some implementations, the user portal 122 and the treatment apparatus 102 may each operate from a user location geographically separate from a location of the clinical portal 124. For example, the user portal 122 and the treatment apparatus 102 may be used as part of an in-home rehabilitation system, which may be aided remotely by using the clinical portal 124 at a centralized location, such as a clinic or a call center.

In some implementations, the clinical portal 124 may be one of several different terminals (e.g., computing devices) that may be physically, virtually or electronically grouped together, for example, in one or more call centers or at one or more healthcare professionals' offices. In some implementations, multiple instance of the clinical portal 124 may be distributed geographically. In some implementations, a person may work as an assistant remotely from any conventional office infrastructure, including a home office. Such remote work may be performed, for example, where the clinical portal 124 takes the form of a computer and/or telephone. This remote work functionality may allow for work-from-home arrangements that may include full-time, part-time and/or flexible work hours for an assistant.

Figure 2A:
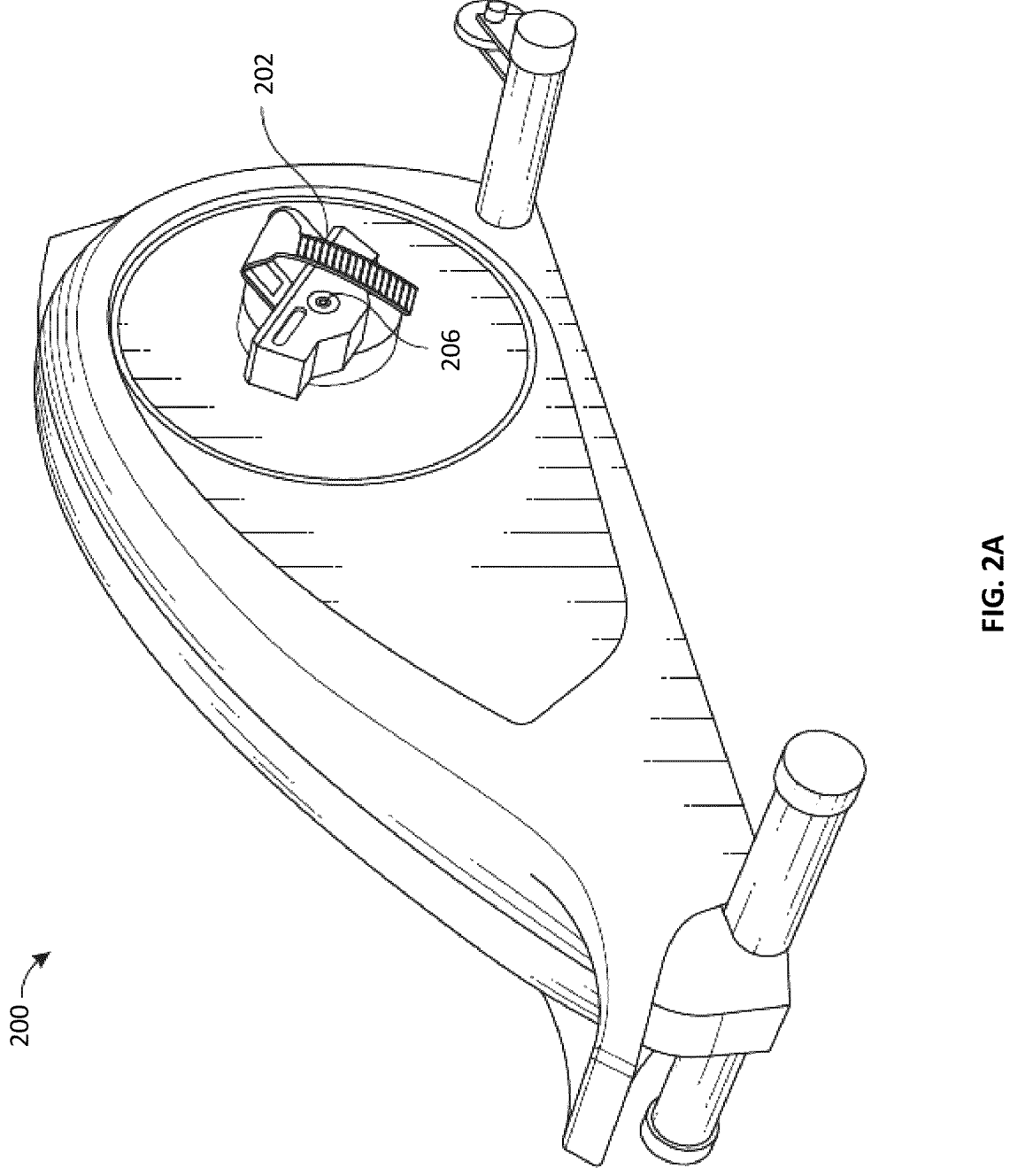
FIGS. 2A and 2B are perspective views of an example of a treatment apparatus included in the system of FIG. 1, in accordance with some implementations of the present disclosure.
Figure 2B:
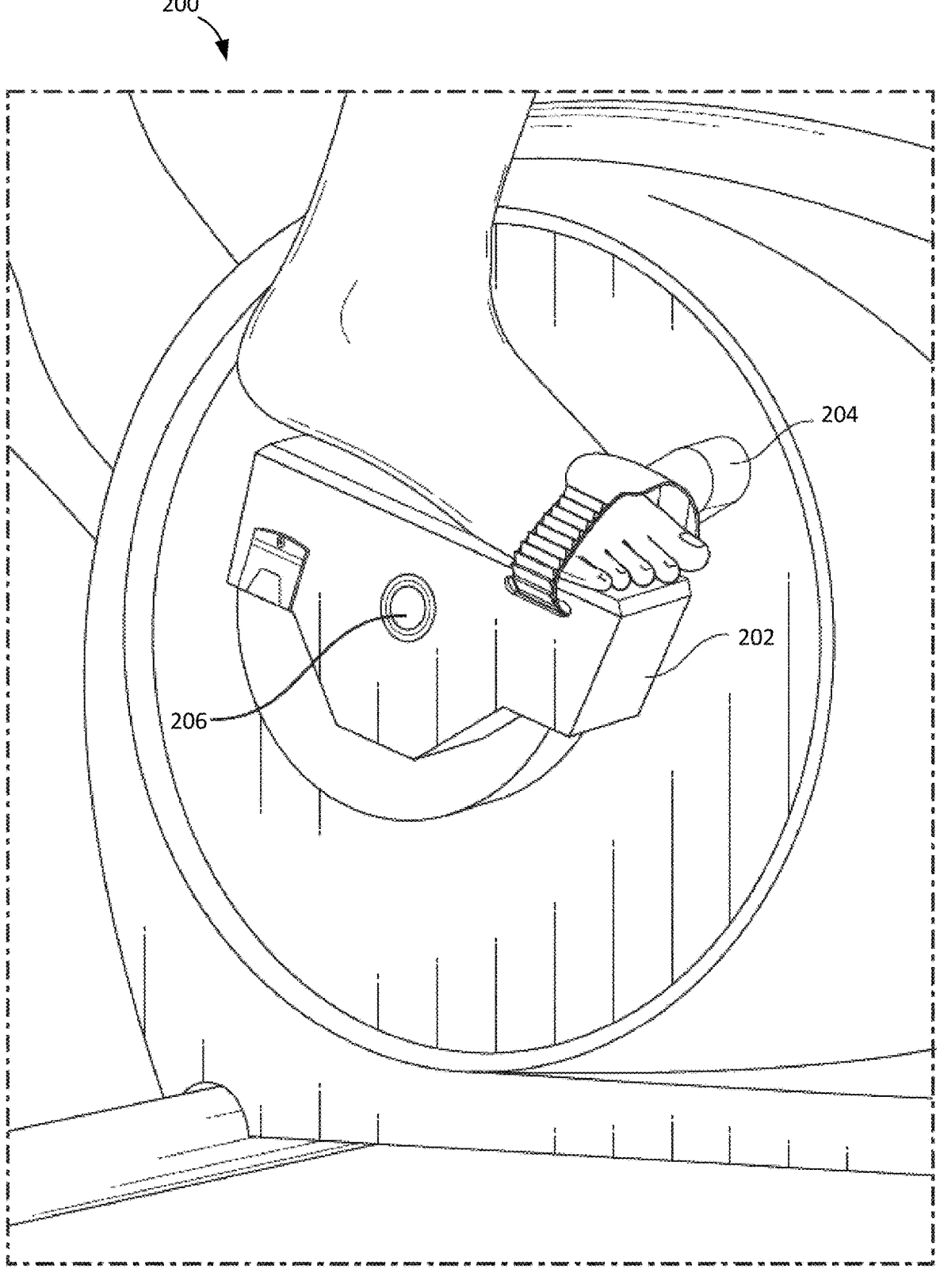

FIGS. 2A and 2B is a perspective view of an example of the treatment apparatus 102. More specifically, FIGS. 2A and 2B show the treatment apparatus 102 in the form of a stationary cycling machine 200, which may be called a stationary bike, for short. The stationary cycling machine 200 includes a set of pedals 202 each attached to a pedal arm 204 for rotation about an axle 206. In some implementations, and as shown in FIGS. 2A and 2B, the pedals 202 are movable on the pedal arms 204 in order to adjust a range of motion used by a user in pedaling. For example, the pedals 202 being located inwardly toward the axle 206 corresponds to a smaller range of motion than when the pedals 202 are located outwardly away from the axle 206.

The treatment apparatus 102 may also include an actuator (e.g., an electric motor). The actuator may be used, for example, for moving body parts of the user and/or for resisting forces by the user. The treatment apparatus 102 may also include one or more integrated sensors. The integrated sensors may measure one or more operating attributes of the treatment apparatus 102 (e.g., force, position, speed, velocity, and the like). In some implementations, the integrated sensors may include a position sensor configured to measure at least one of a linear motion or an angular motion of a body part of the user. For example, an integrated sensor in the form of a position sensor may measure a distance that the user is able to move a part of the treatment apparatus 102, where such distance may correspond to or translate into a range of motion that the user's body part is able to achieve. In some implementations, the integrated sensors may include a force sensor configured to measure a force applied by the user. For example, an integrated sensor in the form of a force sensor may measure a force or weight the user, using a particular body part, is able to apply to the treatment apparatus 102. The one or more integrated sensors may communicate wirelessly to the stationary cycling machine 200 and/or the user computing device 108.

Figure 3:
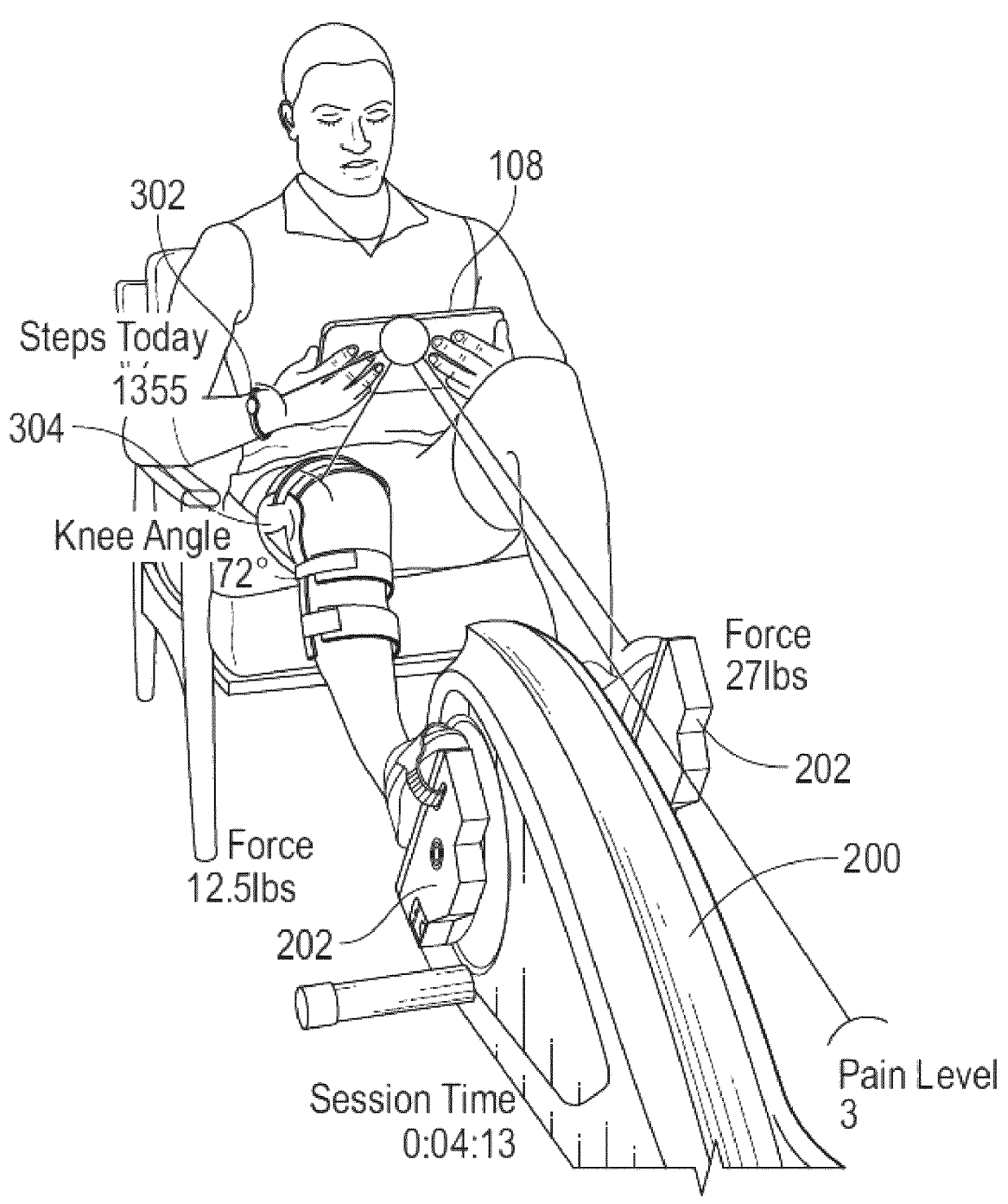
FIG. 3 is a perspective view of an example of a user using the treatment apparatus of FIGS. 2A and 2B, in accordance with some implementations of the present disclosure.

FIG. 3 shows a user using the stationary cycling machine 200 of FIG. 2, and showing sensors and various data parameters connected to the user computing device 108. The user computing device 108 may be a tablet computer or smartphone, or a phablet, such as an iPad, an iPhone, an Android device, a Surface tablet, or any other electronic device held manually by the user. In some implementations, the user computing device 108 may be embedded within or attached to the stationary cycling machine 200, obviating the need for the user to hold the user computing device 108 manually, other than for the possible purpose of interacting with it. FIG. 3 shows the user wearing an ambulation sensor 302 on their wrist, with a note showing "STEPS TODAY 1355", indicating that the ambulation sensor 302 has recorded and transmitted that step count to the user computing device 108. FIG. 3 also shows the user wearing a goniometer 304 on their right knee, with a note showing "KNEE ANGLE 72°," indicating that the goniometer 304 is measuring and transmitting that knee angle to the user computing device 108. FIG. 3 also shows a right side of one of the pedals 202 with a pressure sensor showing "FORCE 12.5 lbs.," indicating that the right pedal pressure sensor is measuring and transmitting that force measurement to the user computing device 108. FIG. 3 also shows a left side of one of the pedals 202 with a pressure sensor showing "FORCE 27 lbs.," indicating that the left pedal pressure sensor is measuring and transmitting that force measurement to the user computing device 108. FIG. 3 also shows other user data, such as an indicator of "SESSION TIME 0:04: 13," indicating that the user has been using the stationary cycling machine 200 for 4 minutes and 13 seconds. This session time may be determined by the user computing device 108 based on information received from the stationary cycling machine 200. FIG. 3 also shows an indicator showing "PAIN LEVEL 3." Such a pain level may be obtained from the user in response to a solicitation or inquiry, such as a question, presented upon the user computing device 108.

Figure 4:
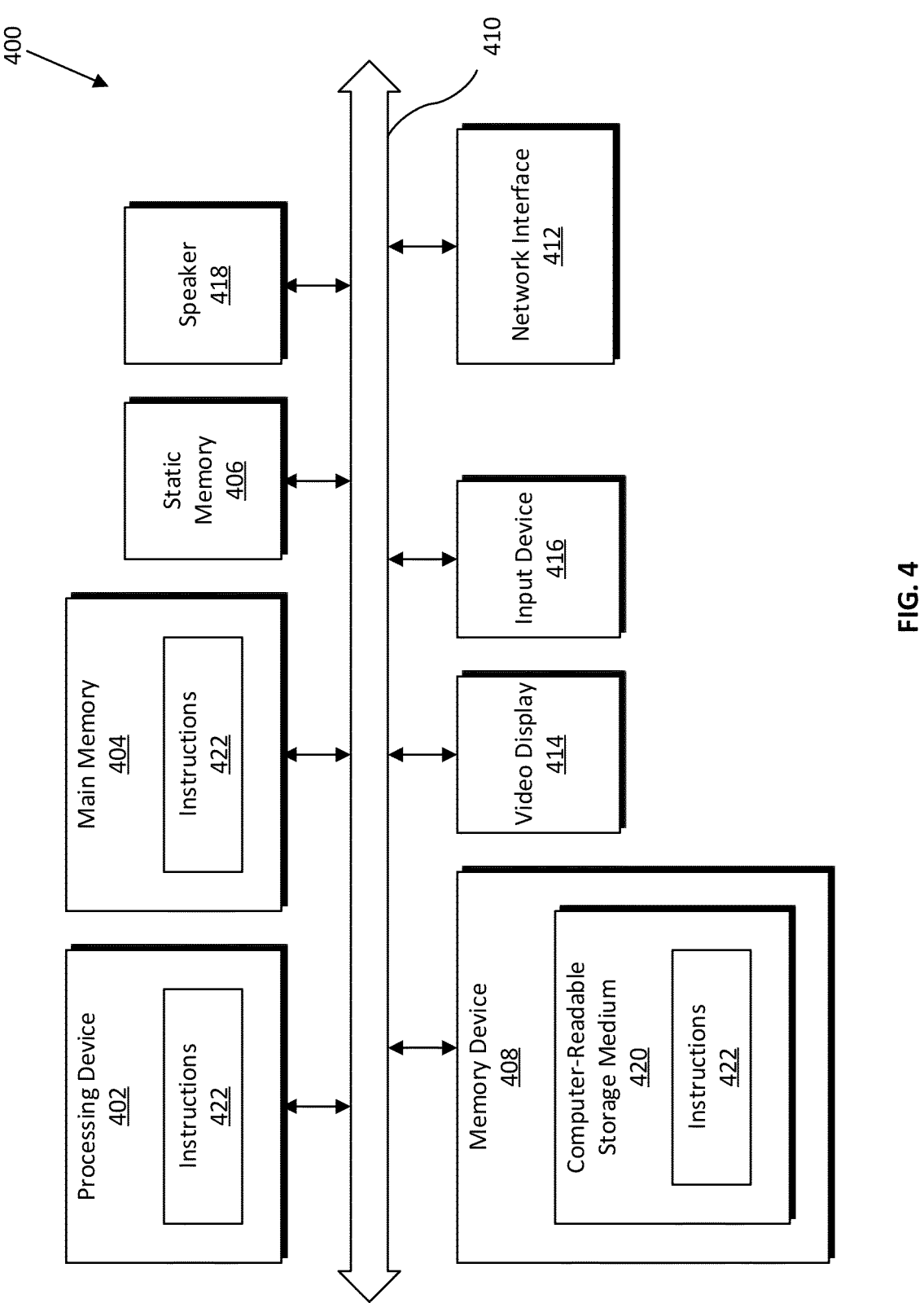
FIG. 4 is a block diagram of an example of a computer system, in accordance with some implementations of the present disclosure.

FIG. 4 is a block diagram of an example of a computer system 400 which can perform any one or more of the methods described herein, in accordance with one or more aspects of the present disclosure. In one example, the computer system 400 may include a computing device and correspond to one or more of the server 106 (including the artificial intelligence engine 116), the user computing device 108, the clinical computing device 110, or any suitable component of FIG. 1. The computer system 400 may be capable of executing instructions implementing the one or more machine learning models 118 of the artificial intelligence engine 116 of FIG. 1. The computer system 400 may be connected (e.g., networked) to other computer systems in a LAN, an intranet, an extranet, or the Internet, including via the cloud or a peer-to-peer network. The computer system 400 may operate in the capacity of a server in a client-server network environment. The computer system 400 may be a personal computer (PC), a tablet computer, a wearable (e.g., wristband), a set-top box (STB), a personal Digital Assistant (PDA), a mobile phone, a smartphone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 400 (one example of a "computing device") illustrated in FIG. 4 includes a processing device 402, a main memory 404 (e.g., read-only memory (ROM), flash memory, solid state drives (SSDs), dynamic random access memory (DRAM) such as synchronous DRAM (SDRAM)), a static memory 406 (e.g., flash memory, solid state drives (SSDs), static random access memory (SRAM)), and a memory device 408, which communicate with each other via a bus 410.

The processing device 402 represents one or more general-purpose processing devices such as a microprocessor, central processing unit, or the like. More particularly, the processing device 402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 402 may also be one or more special-purpose processing devices such as an application specific integrated circuit (ASIC), a system on a chip, a field programmable gate array (FPGA), a digital signal processor (DSP), network processor, or the like. The processing device 402 may be configured to execute instructions for performing any of the operations and steps discussed herein.

The computer system 400 illustrated in FIG. 4 further includes a network interface device 412. The computer system 400 also may include a video display 414 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 416 (e.g., a keyboard and/or a mouse or a gaming-like control), and one or more speakers 418 (e.g., a speaker). In one illustrative example, the video display 414 and the input device(s) 416 may be combined into a single component or device (e.g., an LCD touch screen).

The memory device 408 may include a computer-readable storage medium 420 on which the instructions 422 embodying any one or more of the methods, operations, or functions described herein is stored. The instructions 422 may also reside, completely or at least partially, within the main memory 404 and/or within the processing device 402 during execution thereof by the computer system 400. As such, the main memory 404 and the processing device 402 also constitute computer-readable media. The instructions 422 may further be transmitted or received over a network via the network interface device 412.

While the computer-readable storage medium 420 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying out a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Figure 5:
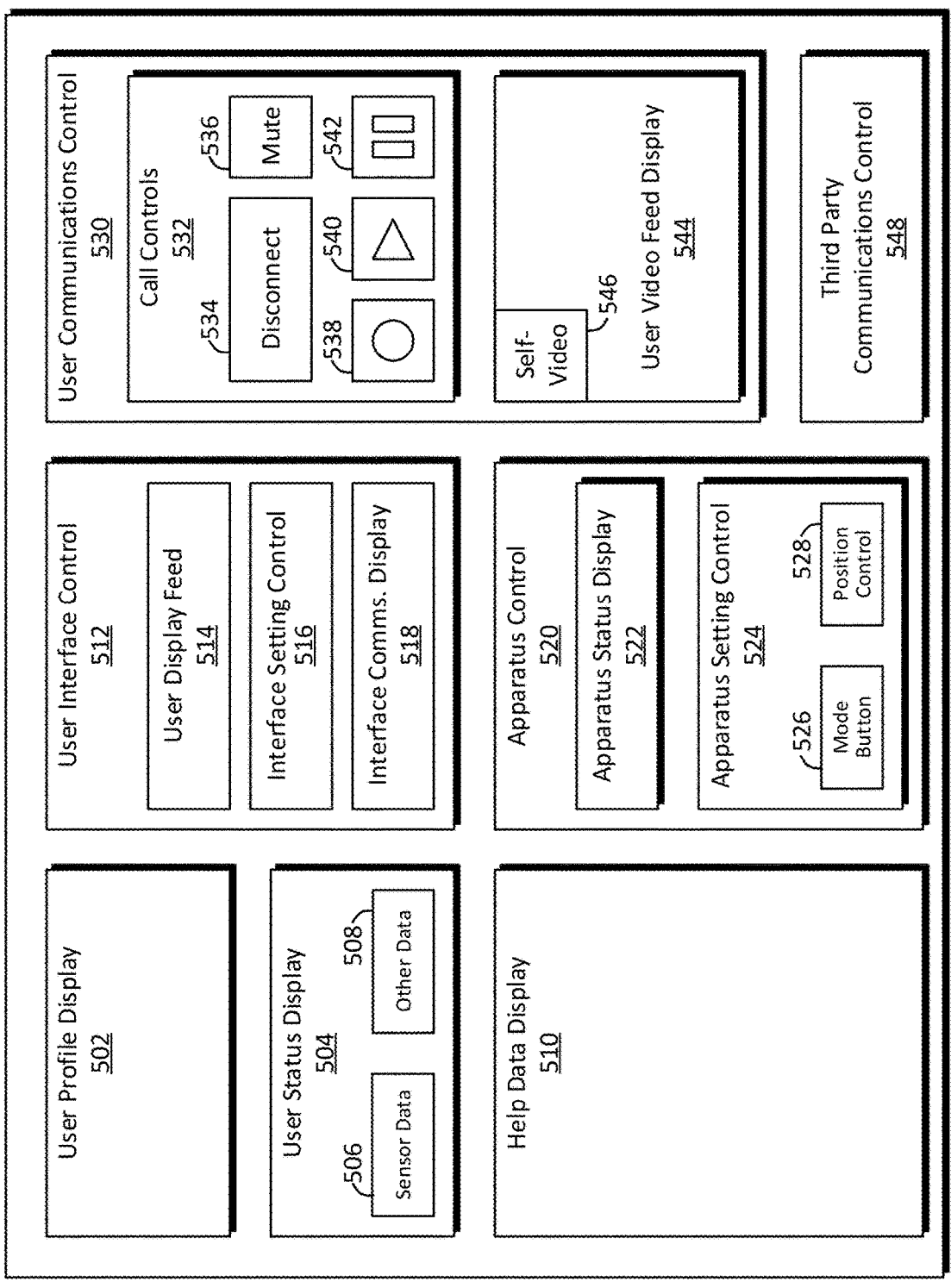
FIG. 5 is a diagram of an example of an overview display of a clinical portal included in the system of FIG. 1, in accordance with some implementations of the present disclosure.

FIG. 5 is a diagram of an example of an overview display 500 of the clinical portal 124. Specifically, the overview display 500 presents several different controls and interfaces for the assistant to remotely assist a user with using the user portal 122 and/or the treatment apparatus 102. This remote assistance functionality may comprise a type of functionality present in telemedicine systems.

Specifically, the overview display 500 includes a user profile display 502 presenting biographical information regarding a user using the treatment apparatus 102. The user profile display 502 may take the form of a portion or region of the overview display 500, as shown in FIG. 5, although the user profile display 502 may take other forms, such as a separate screen or a popup window. In some implementations, the user profile display 502 may include a limited subset of the user's biographical information, health-related information, or both. More specifically, the data presented upon the user profile display 502 may depend upon the assistant's need for that information. For example, a healthcare professional assisting the user with a medical issue may be provided with medical history information regarding the user, whereas a technician troubleshooting an issue with the treatment apparatus 102 may be provided with a much more limited set of information regarding the user. The technician, for example, may be given only the user's name. The user profile display 502 may include pseudonymized data and/or anonymized data or use any privacy enhancing technology to prevent confidential user data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the user may be deemed a "data subject."

In some implementations, the user profile display 502 may present information regarding the treatment plan for the user to follow in using the treatment apparatus 102. Such treatment plan information may be limited to an assistant who is a healthcare professional, such as a doctor or physical therapist. For example, a healthcare professional assisting the user with an issue regarding the treatment regimen may be provided with treatment plan information, whereas a technician troubleshooting an issue with the treatment apparatus 102 may not be provided with any information regarding the user's treatment plan.

In some implementations, one or more recommended treatment plans and/or excluded treatment plans may be presented in the user profile display 502 to the assistant. The one or more recommended treatment plans and/or excluded treatment plans may be generated by the artificial intelligence engine 116 of the server 106 and received from the server 106 in real-time during, inter alia, a telemedicine session. An example of presenting the one or more recommended treatment plans and/or ruled-out treatment plans is described below with reference to FIG. 10

The overview display 500 illustrated in FIG. 5 also includes a user status display 504 presenting status information regarding a user using the treatment apparatus 102. The user status display 504 may take the form of a portion or region of the overview display 500, as shown in FIG. 5, although the user status display 504 may take other forms, such as a separate screen or a pop-up window. The user status display 504 includes sensor data from one or more of the external sensors and/or from one or more internal sensors of the treatment apparatus 102. In some implementations, the user status display 504 may present other data 508 regarding the user, such as last reported pain level, or progress within a treatment plan.

The example overview display 500 shown in FIG. 5 also includes a help data display 510 presenting information for the health professional to use in assisting the user. The help data display 510 may take the form of a portion or region of the overview display 500, as shown in FIG. 5. The help data display 510 may take other forms, such as a separate screen or a pop-up window. The help data display 510 may include, for example, presenting answers to frequently asked questions regarding use of the user portal 122 and/or the treatment apparatus 102. The help data display 510 may also include research data or best practices. In some implementations, the help data display 510 may present scripts for answers or explanations in response to user questions. In some implementations, the help data display 510 may present flow charts or walk-throughs for the healthcare professional to use in determining a root cause and/or solution to a user's problem. In some implementations, the clinical portal 124 may present two or more of the help data display 510, which may be the same or different, for simultaneous presentation of help data for use by the healthcare professional. For example, a first help data display may be used to present a troubleshooting flowchart to determine the source of a user's problem, and a second help data display may present script information for the healthcare professional to read to the user, such information to preferably include directions for the user to perform some action, which may help to narrow down or solve the problem. In some implementations, based upon inputs to the troubleshooting flowchart in the first help data display, the second help data display may automatically populate with script information.

The overview display 500 illustrated in FIG. 5 also includes a user interface control 512 presenting information regarding the user portal 122, and/or for modifying one or more settings of the user portal 122. The user interface control 512 may take the form of a portion or region of the overview display 500, as shown in FIG. 5. The user interface control 512 may take other forms, such as a separate screen or a pop-up window. The user interface control 512 may present information communicated to the clinical portal 124 via one or more of the interface monitor signals. As shown in FIG. 5, the user interface control 512 includes a user display feed 514 of the display presented by the user portal 122. In some implementations, the user display feed 514 may include a live copy of the display screen currently being presented to the user by the user portal 122. In other words, the user display feed 514 may present an image of what is presented on a display screen of the user portal 122. In some implementations, the user display feed 514 may include abbreviated information regarding the display screen currently being presented by the user portal 122, such as a screen name or a screen number. The user interface control 512 may include an interface setting control 516 for the assistant to adjust or to control one or more settings or aspects of the user portal 122. In some implementations, the interface setting control 516 may cause the clinical portal 124 to generate and/or to transmit an interface control signal for controlling a function or a setting of the user portal 122.

In some implementations, the interface setting control 516 may include a collaborative browsing or co-browsing capability for the assistant to remotely view and/or control the user portal 122. For example, the interface setting control 516 may enable the assistant to remotely enter text to one or more text entry fields on the user portal 122 and/or to remotely control a cursor on the user portal 122 using a mouse or touchscreen of the clinical portal 124.

In some implementations, using the user portal 122, the interface setting control 516 may allow the healthcare professional to change a setting that cannot be changed by the user. For example, the user portal 122 may be precluded from enabling access to a language setting in order to prevent a user from inadvertently switching, on the user portal 122, the language used for the displays, whereas the interface setting control 516 may enable the healthcare professional to change the language setting of the user portal 122. In another example, the user portal 122 may not be able to change a font size setting to a smaller size in order to prevent a user from inadvertently switching the font size used for the displays on the user portal 122 such that the display would become illegible or unintelligible to the user, whereas the interface setting control 516 may provide for the healthcare professional to change the font size setting of the user portal 122.

The example on the overview display 500 shown in FIG. 5 also includes an interface communications display 518 showing the status of communications between the user portal 122 and one or more other devices, such as the treatment apparatus 102, the ambulation sensor 302, and the goniometer 304. The interface communications display 518 may take the form of a portion or region of the overview display 500, as shown in FIG. 5. The interface communications display 518 may take other forms, such as a separate screen or a pop-up window. The interface communications display 518 may include controls for the healthcare professional to remotely modify communications with one or more other devices. For example, the healthcare professional may remotely command the user portal 122 to reset communications with one of the other devices, or to establish communications with a new or replacement one of the other devices. This functionality may be used, for example, where the user has a problem with one of the other devices, or where the user receives a new or a replacement one of the other devices.

The example of the overview display 500 illustrates in FIG. 5 also includes an apparatus control 520 for the healthcare professional to view and/or to control information regarding the treatment apparatus 102. The apparatus control 520 may take the form of a portion or region of the overview display 500, as shown in FIG. 5. The apparatus control 520 may take other forms, such as being enabled through or presented on a separate screen or a pop-up window. The apparatus control 520 may include an apparatus status display 522 with information regarding the current status of the treatment apparatus 102. The apparatus status display 522 may present information communicated to the clinical portal 124 via one or more of the apparatus monitor signals. The apparatus status display 522 may indicate whether the treatment apparatus 102 is currently communicating with the user portal 122. The apparatus status display 522 may present other current and/or historical information regarding the status of the treatment apparatus 102.

The apparatus control 520 may include an apparatus setting control 524 for the healthcare professional to adjust or control one or more aspects of the treatment apparatus 102. The apparatus setting control 524 may cause the clinical portal 124 to generate and/or to transmit an apparatus control signal for changing an operating parameter of the treatment apparatus 102 (e.g., a pedal radius setting, a resistance setting, a target RPM, etc.). The apparatus setting control 524 may include, for example, a mode button 526 and a position control 528, which may be used in conjunction for the healthcare professional to place an actuator of the treatment apparatus 102 in a manual mode, after which a setting, such as a position or a speed of the actuator, can be changed using the position control 528. The mode button 526 may provide for a setting, such as a position, to be toggled between automatic and manual modes. In some implementations, one or more settings may be adjustable at any time, but without a necessity of having an associated auto/manual mode. In some implementations, the healthcare professional may change an operating parameter of the treatment apparatus 102, such as a pedal radius setting, while the user is actively using the treatment apparatus 102. Such "on the fly" adjustment may or may not be available to the user using the user portal 122. In some implementations, the apparatus setting control 524 may allow the healthcare professional to change a setting that cannot be changed by the user using the user portal 122. For example, the user portal 122 may be precluded from changing a preconfigured setting, such as a height or a tilt setting of the treatment apparatus 102, whereas the apparatus setting control 524 may provide for the healthcare professional to change the height or tilt setting of the treatment apparatus 102.

The example of the overview display 500 shown in FIG. 5 also includes a user communications control 530 for controlling an audio or an audiovisual communications session with the user portal 122. The communications session with the user portal 122 may comprise a live feed from the clinical portal 124 for presentation on or by the output device of the user portal 122. The live feed may take the form of an audio feed and/or a video feed. In some implementations, the user portal 122 may be configured to provide two-way audio or audiovisual communications with a healthcare professional using the clinical portal 124. Specifically, the communications session with the user portal 122 may include bidirectional (two-way) video or audiovisual feeds, with each of the user portal 122 and the clinical portal 124 presenting video of the other one. In some implementations, the user portal 122 may present video from the clinical portal 124, while the clinical portal 124 presents only audio or the clinical portal 124 presents no live audio or visual signal from the user portal 122. In some implementations, the clinical portal 124 may present video from the user portal 122, while the user portal 122 presents only audio or the user portal 122 presents no live audio or visual signal from the clinical portal 124.

In some implementations, the audio or an audiovisual communications session with the user portal 122 may take place, at least in part, while the user is performing the rehabilitation regimen upon a body part. The user communications control 530 may take the form of a portion or region of the overview display 500, as shown in FIG. 5. The user communications control 530 may take other forms, such as being enabled by or on a separate screen or a pop-up window. The audio and/or audiovisual communications may be processed and/or directed by the clinical portal 124 and/or by another device or devices, such as a telephone system, or a videoconferencing system (e.g., Zoom, WebEx, etc.) used by the healthcare professional while the healthcare professional uses the clinical portal 124. Alternatively or additionally, the audio and/or audiovisual communications may include communications with a third party. For example, the system 100 may enable the assistant to initiate a three-way conversation with the user and a subject matter expert, such as a specialist, regarding use of a particular piece of hardware or software. The example on the user communications control 530 shown in FIG. 5 includes call controls 532 for the healthcare professional to use in managing various aspects of the audio or audiovisual communications with the user. The call controls 532 illustrated in FIG. 5 include a disconnect button 534 for the healthcare professional to end the audio or audiovisual communications session. The call controls 532 illustrated in FIG. 5 also include a mute button 536 to temporarily mute or attenuate an audio or audiovisual signal from the clinical portal 124. In some implementations, the call controls 532 may include other features, such as a hold button (not shown). The call controls 532 may also include one or more record/playback controls, such as a record button 538, a play button 540, and a pause button 542 to control, with the user portal 122, recording and/or playback of audio and/or video from the teleconference session. The user communications control 530 may also include a user video feed display 544 for presenting still and/or video images from the user portal 122, and a self-video display 546 for showing the current image of the healthcare professional using the clinical portal 124. The self-video display 546 may be presented as a picture-in-picture (PiP) format, such PiP format being within a section of the user video feed display 544, as shown in FIG. 5. Alternatively or additionally, the self-video display 546 may be presented separately and/or independently from the user video feed display 544.

The example of the overview display 500 illustrated in FIG. 5 also includes a third party communications control 548 for use in conducting audio and/or audiovisual communications with a third party. The third party communications control 548 may take the form of a portion or region of the overview display 500, as shown in FIG. 5. The third party communications control 548 may take other forms, such as enabling or presenting on a display on a separate screen or a pop-up window. The third party communications control 548 may include one or more controls, such as a contact list and/or buttons or controls to contact a third party regarding use of a particular piece of hardware or software, e.g., a subject matter expert, such as a specialist. The third party communications control 548 may include a conference-calling capability for the third party to simultaneously communicate with both the healthcare professional via the clinical portal 124, and the user via the user portal 122. For example, the system 100 may provide for the assistant to initiate a three-way conversation with the user and the third party.

Maintaining proper body alignment during a treatment session can improve a user's outcome. Maintaining proper body alignment during a treatment session can also reduce pain and discomfort felt by the user during and after the treatment session, and before a future treatment session. Maintaining proper body alignment during a treatment session further can reduce the risk of further aggravating an existing injury and/or causing a new injury to the user. For example, maintaining proper body alignment during a treatment session can ensure a proper amount of pressure is applied to one or more target muscle groups of a user and prevent the application of potentially painful pressure to non-target parts of the user's body. Typically, a user will self-align their body during a treatment session. However, it can be challenging for a user to determine how to properly align their body during a treatment session. For example, the user's lack of medical knowledge may inhibit the user's ability to place their body in a position that does not cause discomfort. Further, in attempting to properly align the user's body, the user's lack of knowledge of the treatment apparatus 102 and/or the user support apparatus 104 may inhibit the user's ability to adjust settings on the treatment apparatus 102 and/or the user support apparatus 104. A healthcare professional can guide the user to properly align their body and/or adjust settings on the treatment apparatus 102 and/or the user support apparatus 104. However, it may be challenging for the healthcare professional to provide such guidance when the healthcare professional is in a location different from the user. Further, it may be technically challenging for the healthcare professional to determine such guidance when the user is using their own user support apparatus. For example, the healthcare professional may be unfamiliar with the dimensions and adjustable settings of a specific chair that a user is using during a treatment session taking place in the user's home. Thus, it may be desirable to generate an alignment plan capable of enabling the aligning of the user's body during a treatment session.

An alignment plan may include a target position of the user's body. The target position may include one or more target locations for one or more parts of the user's body. In some implementations, the target position may include a single target location for one or more parts of the user's body. For example, the alignment plan may include a first single target location for the user's left elbow and a second single target location for the user's right elbow. Alternatively, or additionally, the target position may include multiple target locations for one or more parts of the user's body. For example, the target position may include a range of acceptable target locations for the user's right hand. In some implementations, a target location may include one or more specific coordinates relative to a predefined reference point. For example, a target location may include a set of Cartesian coordinates relative to a predefined reference point on the user support apparatus 104 or the treatment apparatus 102. In other implementations, a target location may include a range of coordinates relative to a predefined reference point.

The alignment plan also may include one or more elements for adjusting the user's body from the user's body's current position in which the user's body is improperly aligned to the target position in which the user's body is properly aligned. In some implementations, the one or more elements may indicate how the user should move their body to adjust their body from its current position to the target position. For example, the one or more elements may include instructions for the user to raise their legs up, keep their knees closer together, move their hands, etc. Alternatively, or additionally, the one or more elements may include one or more directions or control signals for adjusting one or more portion of the treatment apparatus 102 such that the user's body is adjusted from its current position to the target position. For example, the one or more elements may include one or more control signals to increase a resistance setting of the treatment apparatus 102, rotate the pedals 114 to a specific position, decrease a height setting on the treatment apparatus 102, etc. Alternatively or additionally, the one or more elements may include one or more directions for adjusting the user support apparatus 104 such that the user's body is adjusted from its current position to the target position. For example, the one or more elements may include one or more directions to increase the height of a seat, decrease the height of armrests, adjust the position of a seatback, increase the amount of lumbar support, decrease the distance between the user support apparatus 104 and the treatment apparatus 102, etc.

Figure 6A:
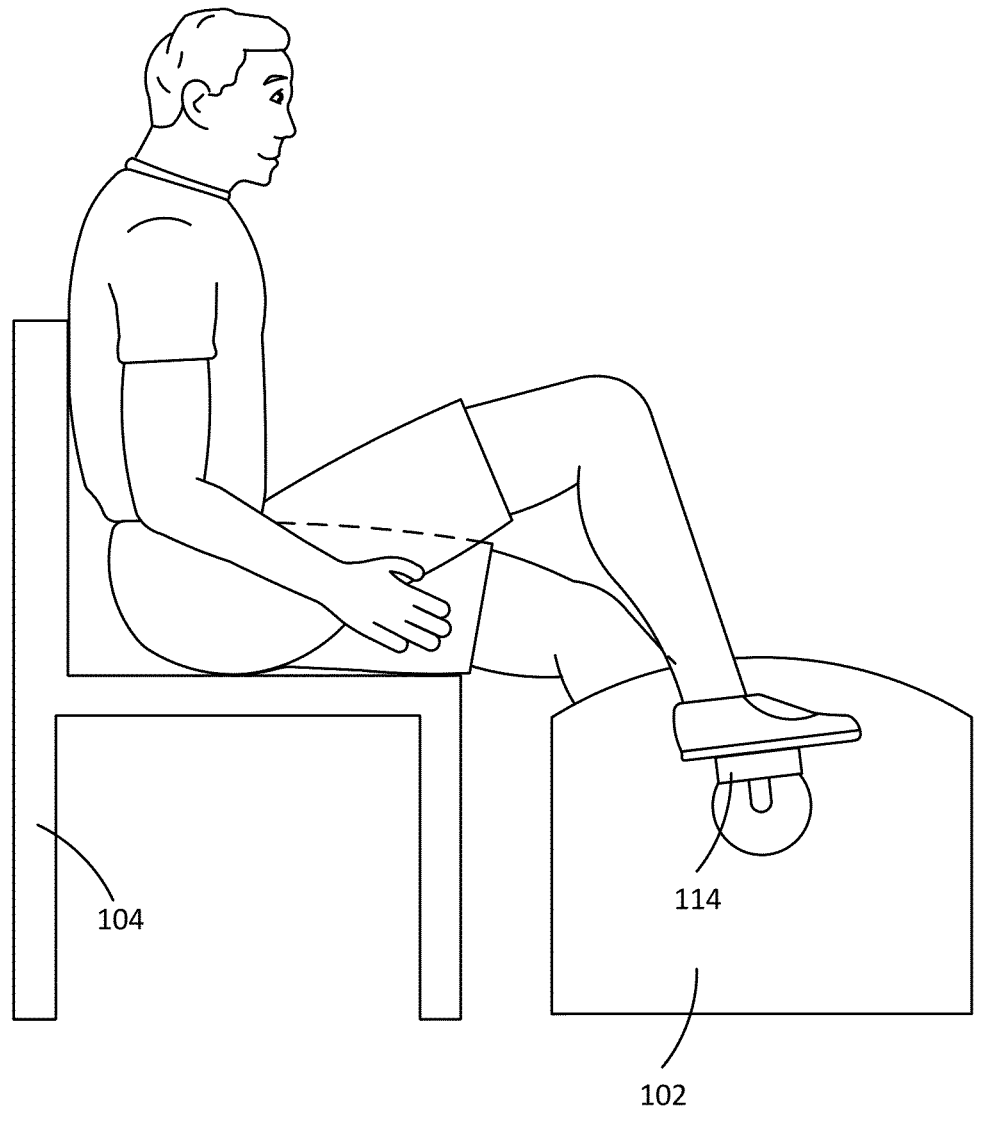
FIGS. 6A and 6B are perspective views of examples of a user using a treatment apparatus included in the system of FIG. 1, in accordance with some implementations of the present disclosure.
Figure 6B:
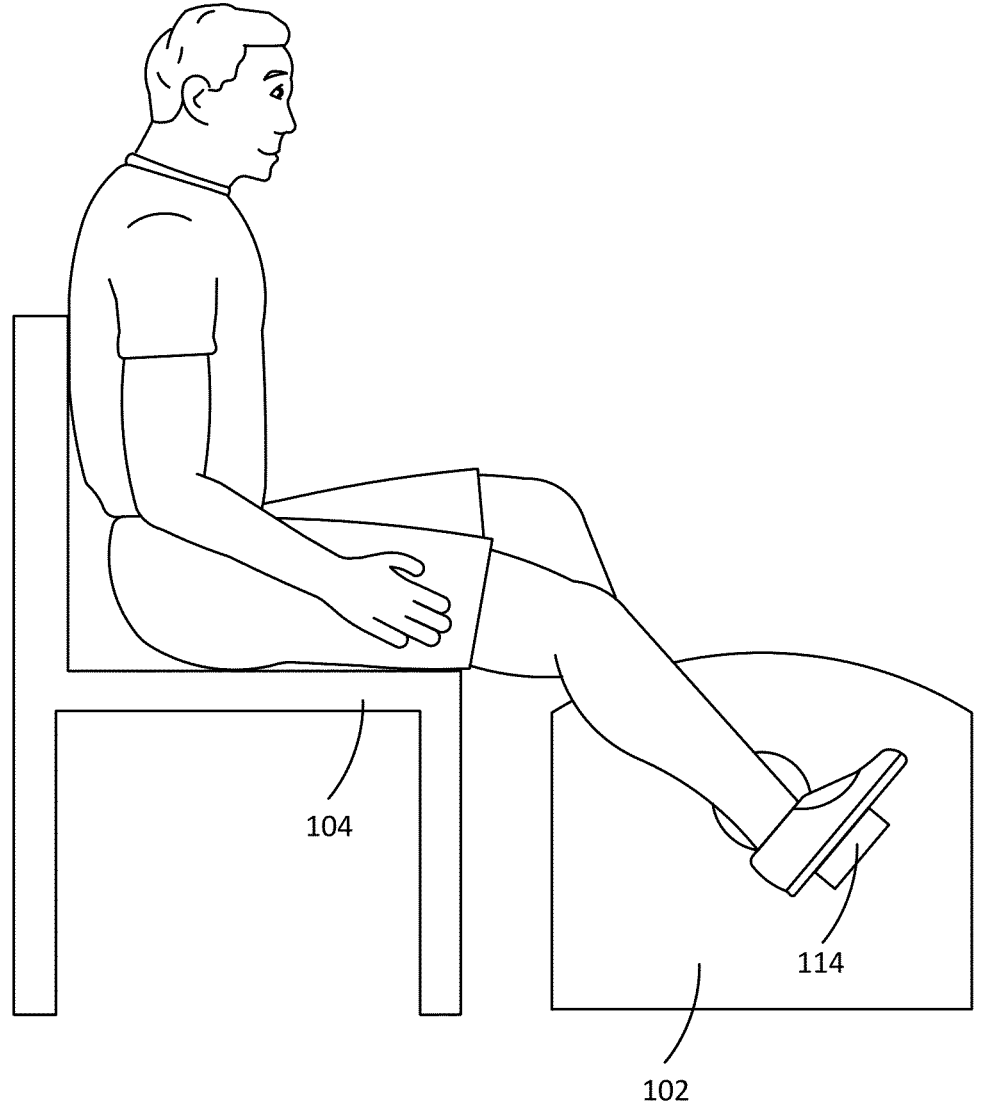
Figure 7:
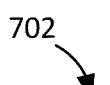
FIG. 7 is a diagram of an example of an overview display of a user portal presenting an illustration of an element included in an instance of an alignment plan, in accordance with some implementations of the present disclosure.

In some implementations, the one or more elements included in the alignment plan may include one or more communications to be presented to the user on the user portal 122 as a visual communication, a tactile communication, an acoustic communication, or a combination thereof. For example, in the situation illustrated in FIGS. 6A and 6B, the user is sitting on the user support apparatus 104 while actuating the pedals 114 on the treatment apparatus 102 as part of a treatment plan. The treatment plan indicates that the bottom of the user's feet should remain positioned parallel to the ground throughout the treatment exercise. As illustrated in FIG. 6A, the bottom of the user's right foot is positioned parallel to the ground when the user's right foot is positioned near the apex of its trajectory. However, as illustrated in FIG. 6B, when the user's right foot is positioned away from the user's body, the bottom of the user's right foot is positioned at a roughly 45° angle to the ground. An example alignment plan generated for the situation illustrated in FIGS. 6A and 6B may indicate that the user should move the user support apparatus 104 closer to the treatment apparatus 102 so that the user can keep their feet positioned parallel to the ground throughout the treatment exercise. FIG. 7 is a diagram of an example of an overview display 702 of the user portal 122, wherein the overview display 702 presents an illustration of an element included in the example alignment plan. The overview display 702 illustrated in FIG. 7 includes text and an image indicating that the user should move the user support apparatus 104 closer to the treatment apparatus 102.

In some implementations, the overview display 702 may include only text or image(s) indicating how the user should move their body. Alternatively or additionally, the overview display 702 may include text and/or image(s) indicating settings for the user to adjust on the treatment apparatus 102. Alternatively or additionally, the overview display 702 may include text and/or image(s) indicating one or more portions for the user to adjust on a user support apparatus 104. In some implementations, the user portal 122 may emit audible instructions indicating how the user should move their body, adjust settings on the treatment apparatus 102, adjust portions of the user support apparatus 104, or a combination thereof. Alternatively or additionally, to presenting the one or more communications to the user on the user portal 122, the one or more communications may be presented to a healthcare professional on the clinical portal 124 as a visual communication, a tactile communication, an acoustic communication, or a combination thereof. For example, during a telemedicine session, the alignment plan may be presented in real-time or near real-time to a healthcare professional on the clinical portal 124. In some implementations, responsive to viewing the alignment plan on the clinical portal 124, a healthcare professional may, to implement the alignment plan, communicate with the user via the clinical portal 124 and the user portal 122. For example, the healthcare professional may instruct the user on how to align their body based on the one or more communications included in the alignment plan. Further, the healthcare professional may instruct the user on how to manually adjust one or more settings on the treatment apparatus 102 and/or the user support apparatus 104 in accordance with the alignment plan. Alternatively or additionally, responsive to viewing the alignment plan on the clinical portal 124, a healthcare professional may provide input to the clinical portal 124 that causes automatic adjustment of one or more settings on the treatment apparatus 102 and/or the user support apparatus 104. For example, the clinical portal 124 may send one or more control signals to the treatment apparatus 102 that cause the treatment apparatus 102 to adjust one or more portions of the treatment apparatus 102 to comply with one or more operating parameters specified in the alignment plan.

In some implementations, the one or more elements included in the alignment plan may cause, without intervention from a healthcare professional, automatic adjustment of one or more settings on the treatment apparatus 102 and/or the user support apparatus 104. For example, the one or more elements may include one or more control signals sent to the treatment apparatus 102 to cause the treatment apparatus 102 to adjust one or more portions of the treatment apparatus 102 to comply with one or more operating parameters specified in the alignment plan. In some implementations, the server 106 may send the alignment plan to the treatment apparatus 102 and/or the user support apparatus 104 (either directly via the communications network 112 or indirectly via the user computing device 108).

In some implementations, the one or more control signals may cause a force to be imparted to one or more pedals 114 of the treatment apparatus 102. For example, in implementations of the treatment apparatus 102 where the pedals 114 move in angular directions (such as the example illustrated in FIG. 2A), the one or more control signals may cause a rotation of the one or more pedals 114 of the treatment apparatus 102. As a further example, in implementations of the treatment apparatus 102 where the pedals 114 move in lateral directions, the one or more control signals may cause a lateral displacement of the pedals 114. In some implementations, the one or more control signals cause the treatment apparatus 102 to modify a volume, a pressure, a resistance, an angle, an angular or rotational velocity, a speed, a time period, or a combination thereof. In some implementations, the one or more control signals may cause the treatment apparatus 102 to adjust a radius of rotation of one or more of the pedals 114, a level of assistance applied by an electric motor, an amount of resistance the electric motor applies to the one or more pedals 114, or a combination thereof.

In some implementations, a user interface (e.g., the user portal 122, the clinical portal 124, or a user interface included in the server 106) may generate an instance of a virtual representation of the targeted portion of the body. The instance of the virtual representation may characterize, in real-time or near real-time, the current location of the targeted portion of the body. Having a virtual representation that characterizes the current location of the targeted portion of the body can aid the user and/or a healthcare professional in implementing an alignment plan. For example, when a user video feed does not provide a clear view of the targeted portion of the user's body, the virtual representation may enable a healthcare professional to identify the current location of the targeted portion of the body. As a further example, the virtual representation may provide live feedback that aids the user in adjusting their body in accordance with communications included in an alignment plan.

Different users may have different attributes. As a first example, a first user may be more flexible than a second user. Thus, an alignment plan that does not cause any discomfort when implemented by the first user may cause discomfort when implemented by the second user. As a second example, the first and second users may have different body types. Thus, an alignment plan that causes a proper alignment of the first user's body during a treatment session may not properly align the second user's body during a treatment session. Generating alignment plans for a user having certain attributes (e.g., vital-sign or other measurements; performance-based; demographic; psychographic; geographic; diagnostic; measurement- or test-based; medically historic; behaviorally historic; cognitive; etiologic; cohort-associative; differentially diagnostic; surgical; physically therapeutic; pharmacologic; or other treatment(s) recommended; etc.) may be a technically challenging problem. For example, a multitude of information may be considered when generating an alignment plan, and such consideration may result in inefficiencies and inaccuracies in the alignment plan selection process. In a rehabilitative setting, some of the multitude of information considered may include attributes of the user such as personal information, performance information, and measurement information. Personal information may include, e.g., demographic, psychographic or other information, such as an age, a weight, a gender, a height, a body mass index, a medical condition, a familial medication history, an injury, a medical procedure, a medication prescribed, or any combination thereof. Performance information may include, e.g., an elapsed time of using the treatment apparatus 102, an amount of force exerted on a portion of the treatment apparatus 102, a range of motion achieved on the treatment apparatus 102, a movement speed of a portion of the treatment apparatus 102, an indication of a plurality of pain levels using the treatment apparatus 102, or any combination thereof. Measurement information may include, e.g., a vital sign, a respiration rate, a heartrate, a temperature, a blood pressure, or any combination thereof. Correlating a specific user's attributes with known data for a cohort of other users enables the generation of an alignment plan that results in efficiently aligning the user's body during a treatment in a manner that avoids causing the user pain. Therefore, it may be desirable to process the attributes of a multitude of users, the alignment plans performed by those users, and the results of the alignment plans for those users.

Accordingly, systems and methods, such as those described herein, that use artificial intelligence and/or machine learning to generate alignment plans, may be desirable. For example, the machine learning models 118 may be trained to assign users to certain cohorts based on their attributes, select alignment plans using real-time and historical data correlations involving user cohort-equivalents, and control the treatment apparatus 102, among other things. The one or more machine learning models 118 may be generated by the training engine 120 and may be implemented in computer instructions executable by one or more processing devices of the training engine 120 and/or the server 106. To generate the one or more machine learning models 118, the training engine 120 may train the one or more machine learning models 118. The one or more machine learning models 118 may be used by the artificial intelligence engine 116.

To train the one or more machine learning models 118, the training engine 120 may use a training data set of a corpus of the attributes of the users that used the treatment apparatus 102 to perform alignment plans, the details (e.g., alignment protocol including parameters/configurations/settings of the treatment apparatus 102 and/or the user support apparatus 104) of the alignment plans performed by the users using the treatment apparatus 102, and the results of the alignment plans performed by the users. The one or more machine learning models 118 may be trained to match patterns of attributes of a user with attributes of other users assigned to a particular cohort. The term "match" may refer to an exact match, or to correspondences, associations, relationships, approximations or other mathematical, linguistic and other non-exact matches, including, e.g., a correlative match, a substantial match, a partial match, an associative match, a relational match, etc. The one or more machine learning models 118 may be trained to receive the attributes of a user as input, to map the attributes to attributes of user assigned to a cohort, and to select an alignment plan from that cohort. The one or more machine learning models 118 may also be trained to control, based on the alignment plan, the treatment apparatus 102.

Different machine learning models 118 may be trained to recommend different treatment plans for different desired results. For example, one machine learning model may be trained to recommend alignment plans for the most effective image data capturing, while another machine learning model may be trained to recommend alignment plans, wherein the recommendation of the alignment plan is based on reducing user discomfort.

Using training data that includes training inputs and corresponding target outputs, the one or more machine learning models 118 may refer to model artifacts created by the training engine 120. The training engine 120 may find patterns in the training data wherein such patterns map the training input to the target output, and generate the machine learning models 118 that capture these patterns. In some implementations, the artificial intelligence engine 116 and/or the training engine 120 may reside on another component (e.g., the user computing device 108, the clinical computing device 110, etc.) depicted in FIG. 1.

The one or more machine learning models 118 may comprise, e.g., a single level of linear or non-linear operations (e.g., a support vector machine [SVM]) or the machine learning models 118 may be a deep network, i.e., a machine learning model comprising multiple levels of non-linear operations. Examples of deep networks include neural networks, and neural networks may include generative adversarial networks, convolutional neural networks, recurrent neural networks with one or more hidden layers, and fully connected neural networks (e.g., wherein each neuron may transmit its output signal to the input of the remaining neurons, as well as to itself). For example, the machine learning model may include numerous layers and/or hidden layers that use various neurons to perform calculations (e.g., dot products).

Figure 8:
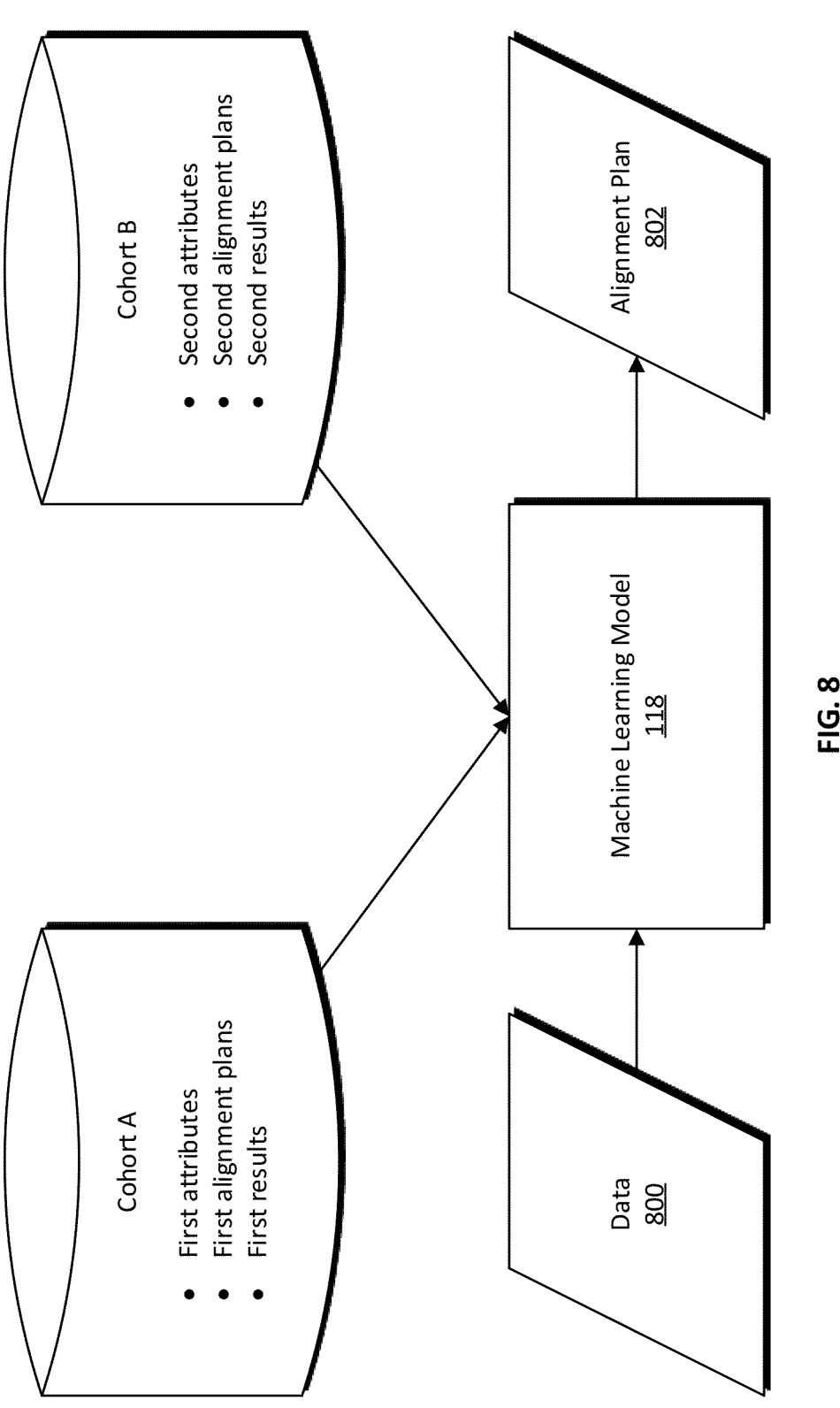
FIG. 8 is a block diagram of an example of training a machine learning model to output, based on data pertaining to a user, an alignment plan for the user, in accordance with some implementations of the present disclosure.

FIG. 8 shows a block diagram of an example of training the machine learning model 118 to output, based on data 800 pertaining to the user, an alignment plan 802 for the user according to the present disclosure. Data pertaining to other users may be received by the server 106. The other users may have used various treatment apparatuses to perform treatment sessions. The data may include attributes of the other users, the details of the alignment plans performed by the other user, and/or the results of performing the alignment plans (e.g., an amount of pain or discomfort experienced by the user, an amount of increase or decrease in muscle strength of a portion of users' bodies, an amount of increase or decrease in range of motion of a portion of users' bodies, etc.).

As depicted in FIG. 8, the data has been assigned to different cohorts. Cohort A includes data for users having similar first attributes, first alignment plans, and first results. Cohort B includes data for users having similar second attributes, second alignment plans, and second results. For example, cohort A may include first attributes of users in their twenties without any medical conditions, and if, for example, such users underwent surgery for a broken limb, such cohort A users' alignment plans may include a first alignment protocol (e.g., the values for the properties, configurations, and/or settings of the treatment apparatus 102 are set to X (where X is a numerical value). Further, cohort B may include second attributes of users in their sixties with arthritis, and if, for example, such users also underwent surgery for a broken limb, such cohort B users' alignment plans may include a second alignment protocol (e.g., the values for the properties, configurations, and/or settings of the treatment apparatus 102 are set to Y (wherein Y is a numerical value)).

As further depicted in FIG. 8, cohort A and cohort B may be included in a training dataset used to train the machine learning model 118. The machine learning model 118 may be trained to match a pattern between one or more attributes for each cohort and to output the alignment plan that provides the result, i.e., the best match. Accordingly, when the data 800 for a new user is input into the trained machine learning model 118, the trained machine learning model 118 may match the one or more attributes included in the data 800 with one or more attributes in either cohort A or cohort B and output the appropriate alignment plan 802.

Figure 9:
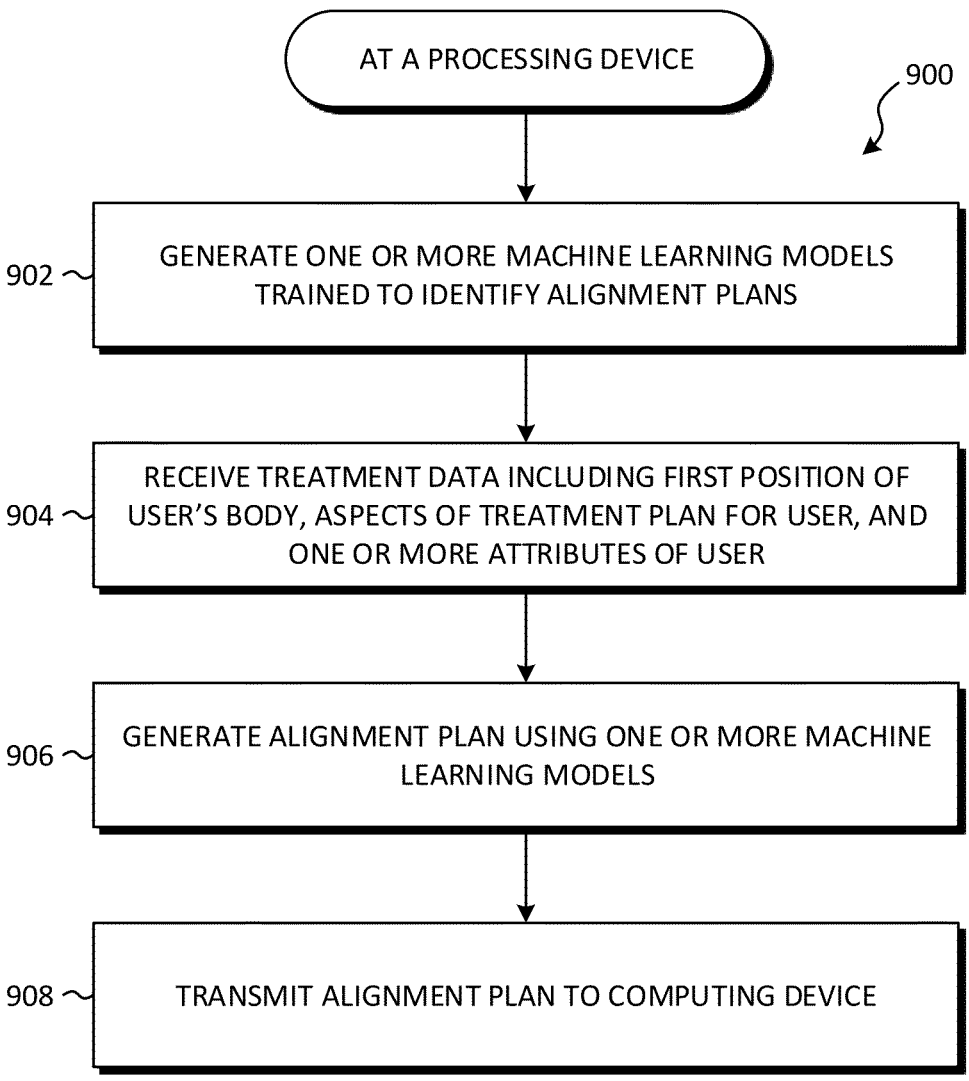
FIG. 9 is a flow diagram of an example of a method for generating an alignment plan capable of enabling, during a treatment session, the aligning of a user's body, in accordance with some implementations of the present disclosure.

FIG. 9 is a flow diagram of an example of a method 900 for generating an alignment plan capable of enabling, during a treatment session, the aligning a user's body. The method 900 is performed by processing logic that may include hardware (circuitry, dedicated logic, etc.), software (such as is run on a general-purpose computer system, a dedicated machine, or a computing device of any kind (e.g., IoT node, wearable, smartphone, mobile device, etc.)), or a combination of both. The method 900 and/or each of its individual functions (including "methods," as used in object-oriented programming), routines, subroutines, or operations may be performed by one or more processors of a computing device (e.g., any component of FIG. 1, such as server 106 executing the artificial intelligence engine 116). In certain implementations, the method 900 may be performed by a single processing thread. Alternatively, the method 900 may be performed by two or more processing threads, wherein each thread implements one or more individual functions, routines, subroutines, or operations of the method 900.

For simplicity of explanation, the method 900 is depicted in FIG. 9 and described as a series of operations performed by the server 106. However, operations in accordance with this disclosure can occur in various orders and/or concurrently, and/or with other operations not presented and described herein. For example, the operations depicted in the method 900 in FIG. 9 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented via a state diagram or event diagram as a series of interrelated states.

At block 902, the server 106 generates one or more machine learning models trained to identify alignment plans. For example, using any of the training methods previously described above such as the methods described in relation to FIG. 8, the artificial intelligence engine 116 may further use the training engine 120 to train the one or more machine learning models 118 to identify alignment plans.

At block 904, the server 106 receives treatment data. The treatment data may include a first position of the user's body. The first position may represent the current (or recently-current) position of the user's body. In some implementations, the server 106 may receive the first position of the user's body from, for example, a camera, a RADAR sensing system, a LIDAR sensing system, an acoustic sensing system, a thermal sensing system, an ultrasonic sensing system, the goniometer 304, or a combination thereof. The treatment data also may include one or more attributes of the user. For example, the treatment data may include any of or all the personal information, performance information, and/or measurement information previously described above. The treatment data also may include aspects of a treatment plan for the user. A treatment plan (e.g., a prehabilitation plan, a rehabilitation plan, etc.) may include one or more exercise sessions that may be performed, using the treatment apparatus 102, by the user. An exercise session may include one or more treatment exercises the user can complete to strengthen, make more pliable, reduce inflammation and/or swelling in, and/or increase endurance in an area of the body; tasks the user can complete; a start date and end date for a treatment plan; goals relating to a treatment plan (e.g., dietary goals, sleep goals, exercise goals, etc.); descriptions and/or identifiers of a medical procedure that was performed (or that is to be performed) on the user; and the like. The one or more exercises may, for example, include a set of pedaling sessions to be performed using the treatment apparatus 102, a set of joint extension sessions, a set of flex sessions, a set of walking sessions, a set of heartrates per pedaling session and/or walking session, and the like. For example, a user undergoing prehabilitation may perform a pedaling session as part of a prehabilitation plan created to assist a patient in strengthening or improving a condition of one or more body parts which may be affected by an upcoming surgery, to strengthen or improve a condition of one or more body parts, wherein the strengthening or improving is for the purpose of reducing the chance of an injury at a later time period, and the like.

In some implementations, the treatment data may include one or more attributes of the treatment apparatus 102. For example, the server 106 may receive data indicating a position of the treatment apparatus 102, one or more settings of the treatment apparatus 102, a current revolutions per minute of a rotating member (e.g., such as a wheel) of the treatment apparatus 102, a resistance setting of the treatment apparatus 102, an angular or rotational velocity of the treatment apparatus 102 or components thereof, other suitable attributes of the treatment apparatus 102, or a combination thereof.

In some implementations, the treatment data may include one or more attributes of the user support apparatus 104. For example, the server 106 may receive data indicating one or more positions of the user support apparatus 104, one or more settings of the user support apparatus 104, or a combination thereof. The user support apparatus 104 may include a plurality of different portions. For example, the user support apparatus 104 may include a seatback, a seat rest, an armrest, a harness, a balance board, a footrest, or a combination thereof. In some implementations, the treatment data may include one or more attributes of a portion of the user support apparatus 104. For example, the server 106 may receive data indicating a range of selectable positions for an adjustable seatback on a weight bench as well as the current position of the adjustable seatback.

At block 906, the server 106 generates the alignment plan using the one or more machine learning models generated at block 902. The server 106 generates the alignment plan based on at least the aspects of the treatment plan and at least one of the one or more attributes of the user. In some implementations, the server 106 may further generate the alignment plan based on the first position of the user's body. The alignment plan comprises at least, first, a target position of the user's body and, second, one or more elements for adjusting the user's body from the first position to the target position.

At block 908, the server 106 transmits the alignment plan to a computing device. For example, the server 106 transmits the alignment plan to the user computing device 108, the clinical computing device 110, another computing device, or a combination thereof.

Depending on what result is desired, the artificial intelligence engine 116 may be trained to output several treatment plans. For example, one result may include recovering to a threshold level (e.g., 75% range of motion) in a fastest amount of time, while another result may include fully recovering (e.g., 100% range of motion) regardless of the amount of time. Another result may include recovering while not exceeding a threshold level for bruising (e.g., at or below a specific bruising level) between treatment sessions, while another result may include recovering while not exceeding a threshold level for bruising during a treatment session.

The artificial intelligence engine 116 may compare the following (i) expected information, which pertains to the user while the user uses the treatment apparatus 102 to perform the treatment plan to (ii) the measurement information (e.g., indicated by the treatment information), which pertains to the user while the user uses the treatment apparatus 102 to perform the treatment plan. The expected information may include one or more vital signs of the user, a respiration rate of the user, a heartrate of the user, a temperature of the user, a blood pressure of the user, other suitable information of the user, or a combination thereof. The artificial intelligence engine 116 may determine that the treatment plan is optimal for the particular user (i.e., the user is having a desired rehabilitation result) if one or more parts or portions of the measurement information are within an acceptable range associated with one or more corresponding parts or portions of the expected information (e.g., within one or more thresholds). Conversely, the artificial intelligence engine 116 may determine that the treatment plan is not optimal for the particular user (i.e., the user is not having a desired rehabilitation result) if one or more parts or portions of the measurement information are outside of the range associated with one or more corresponding parts or portions of the expected information (e.g., outside of the one or more thresholds).

In some implementations, the system 100 may interact with the user portal 122 to provide treatment plan input indicating one or more modifications to the treatment plan and/or to one or more attributes of the treatment apparatus 102 device if the artificial intelligence engine 116 determines to modify the treatment plan and/or the one or more attributes of the treatment apparatus 102. For example, the user portal 122 may provide input indicating an increase or decrease in the resistance setting of the treatment apparatus 102, an increase or decrease in an amount of time the user is required to use the treatment apparatus 102 according to the treatment plan, or other suitable modification to the one or more attributes of the treatment apparatus 102.

In some implementations, the systems and methods described herein may be configured to modify the treatment plan based on one or more modifications indicated by the treatment plan input. Additionally, or alternatively, the systems and methods described herein may be configured to modify the one or more attributes of the treatment apparatus 102 based on the modified treatment plan and/or the treatment plan input. For example, the treatment plan input may indicate to modify the one or more attributes of the treatment apparatus 102 and/or the modified treatment plan may require or indicate adjustments to the treatment apparatus 102 in order for the user to achieve the desired results of the modified treatment plan.

In some implementations, the systems and methods described herein may be configured to receive subsequent treatment data pertaining to the user while the user uses the treatment apparatus 102 to perform the modified treatment plan. For example, after the artificial intelligence engine 116 modifies the treatment plan and/or controls the one or more attributes of the treatment apparatus 102, the user may continue use the treatment apparatus 102 to perform the modified treatment plan. The subsequent treatment data may correspond to treatment data generated while the user uses the treatment apparatus 102 to perform the modified treatment plan. In some implementations, the subsequent treatment data may correspond to treatment data generated while the user continues to use the treatment apparatus 102 to perform the treatment plan, after the healthcare professional has received the treatment information and determined not to modify the treatment plan and/or control the one or more attributes of the treatment apparatus 102.

Based on subsequent (e.g., modified) treatment plan input generated by the artificial intelligence engine 116, the systems and methods described herein may be configured to further modify the treatment plan and/or control the one or more attributes of the treatment apparatus 102. The subsequent treatment plan input may correspond to input provided by the user at the user portal 122, from treatment data corresponding to sensor data from a sensor of a wearable device worn by the user during one of the one or more treatment sessions, from a sensor configured to detect treatment data pertaining to the user, any other desired information, or combination thereof.

The healthcare professional may receive and/or review treatment information continuously or periodically while the user uses the treatment apparatus 102 to perform the treatment plan. Based on one or more trends indicated by the continuously and/or periodically received treatment information, the healthcare professional may determine whether to modify the treatment plan and/or control the one or more attributes of the treatment apparatus 102. For example, the one or more trends may indicate an increase in heart rate or other suitable trends indicating that the user is not performing the treatment plan properly and/or performance of the treatment plan by the user is not having the desired effect.

In some implementations, the systems and methods described herein may be configured to use artificial intelligence and/or machine learning to assign users to cohorts and to dynamically control a treatment apparatus 102 based on the assignment during an adaptive telemedicine session. In some implementations, numerous treatment apparatuses 102 may be provided to users. The treatment apparatuses 102 may be used by the users to perform treatment plans in their residences, at a gym, at a rehabilitative center, at a hospital, or any suitable location, including permanent or temporary domiciles.

In some implementations, the treatment apparatuses 102 may be communicatively coupled to the server 106 (e.g., via the communications network 112). Attributes of the users, including the treatment data, may be collected before, during, and/or after the user perform the treatment plans. For example, the personal information, the performance information, and the measurement information may be collected before, during, and/or after the user performs the treatment plans. The results (e.g., improved performance or decreased performance) of performing each exercise may be collected from the treatment apparatus 102 throughout the treatment plan and after the treatment plan is performed. The parameters, settings, configurations, etc. (e.g., position of pedals 114, amount of resistance, etc.) of the treatment apparatus 102 may be collected before, during, and/or after the treatment plan is performed.

Each attribute of the user, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses 102 and/or any suitable computing device (e.g., the user computing device 108, the clinical computing device 110, the server 106, and the like) over time as the users use the treatment apparatuses 102 to perform the various treatment plans. The data that may be collected may include the attributes of the users, the treatment plans performed by the users, the results of the treatment plans, any of the data described herein, any other suitable data, or a combination thereof.

In some implementations, the data may be processed to group certain users into cohorts. The users may be grouped by users having certain or selected similar attributes, treatment plans, and results of performing the treatment plans. For example, athletic users having no medical conditions who perform a treatment plan (e.g., use the treatment apparatus 102 for 30 minutes a day 5 times a week for 3 weeks) and who fully recover may be grouped into a first cohort. Older users who are classified obese and who perform a treatment plan (e.g., use the treatment apparatus 102 for 10 minutes a day 3 times a week for 4 weeks) and who improve their range of motion by 75 percent may be grouped into a second cohort.

In some implementations, the artificial intelligence engine 116 may include one or more machine learning models 118 that are trained using the cohorts. For example, the one or more machine learning models 118 may be trained to receive an input of attributes of a new user and to output a treatment plan for the user that results in a desired result. The machine learning models 118 may match a pattern between the attributes of the new user and at least one user of the users included in a particular cohort. When a pattern is matched, the machine learning models 118 may assign the new user to the particular cohort and select the treatment plan associated with the at least one user. The artificial intelligence engine 116 may be configured to control, distally and based on the treatment plan, the treatment apparatus 102 while the new user uses the treatment apparatus 102 to perform the treatment plan.

As may be appreciated, the attributes of the new user may change as the new user uses the treatment apparatus 102 to perform the treatment plan. For example, the performance of the user may improve quicker than expected for users in the cohort to which the new user is currently assigned. Accordingly, the machine learning models 118 may be trained to dynamically reassign, based on the changed attributes, the new user to a different cohort that includes users having attributes similar to the now-changed attributes as the new user. For example, a clinically-obese user may lose weight and no longer meet the weight criterion for the initial cohort, result in the user being reassigned to a different cohort with a different weight criterion.

A different treatment plan may be selected for the new user, and the treatment apparatus 102 may be controlled, distally (e.g., which may be referred to as remotely) and based on the different treatment plan, the treatment apparatus 102 while the new user uses the treatment apparatus 102 to perform the treatment plan. Such techniques may provide the technical solution of distally controlling the treatment apparatus 102.

Further, the systems and methods described herein may lead to faster recovery times and/or better results for the users because the treatment plan that most accurately fits their attributes is selected and implemented, in real-time, at any given moment.

Further, the artificial intelligence engine 116 may be trained to output treatment plans that are not optimal i.e., sub-optimal, nonstandard, or otherwise excluded (all referred to, without limitation, as "excluded treatment plans") for the user. For example, if a user has high blood pressure, a particular exercise may not be approved or suitable for the user as it may put the user at unnecessary risk or even induce a hypertensive crisis and, accordingly, that exercise may be flagged in the excluded treatment plan for the user. In some implementations, the artificial intelligence engine 116 may monitor the treatment data received while the user with, for example, high blood pressure, uses the treatment apparatus 102 to perform an appropriate treatment plan and may modify the appropriate treatment plan to include features of an excluded treatment plan that may provide beneficial results for the user if the treatment data indicates the user is handling the appropriate treatment plan without aggravating, for example, the high blood pressure condition of the user.

In some implementations, the treatment plans and/or excluded treatment plans may be presented, during a telemedicine or telehealth session, to a healthcare professional. The healthcare professional may select a particular treatment plan for the user to cause that treatment plan to be transmitted to the user and/or to control, based on the treatment plan, the treatment apparatus 102. In some implementations, to facilitate telehealth or telemedicine applications, including remote diagnoses, determination of treatment plans and rehabilitative and/or pharmacologic prescriptions, the artificial intelligence engine 116 may receive and/or operate distally from the user and the treatment apparatus 102.

In such cases, the recommended treatment plans and/or excluded treatment plans may be presented simultaneously with a video of the user in real-time or near real-time during a telemedicine or telehealth session on the clinical portal 124 of the clinical computing device 110 of a healthcare professional. The video may also be accompanied by audio, text and other multimedia information and/or sensorial or perceptive (e.g., tactile, gustatory, haptic, pressure-sensing-based or electromagnetic (e.g., neurostimulation)).

Presenting the treatment plans generated by the artificial intelligence engine 116 concurrently with a presentation of the user video feed display 544 may provide an enhanced user interface because the healthcare professional may continue to visually and/or otherwise communicate with the user while also reviewing the treatment plans on the same user interface. The enhanced user interface may improve the healthcare professional's experience using the clinical computing device 110 and may encourage the healthcare professional to reuse the user interface. Such a technique may also reduce computing resources (e.g., processing, memory, network) because the healthcare professional does not have to switch to another user interface screen to enter a query for a treatment plan to recommend based on the attributes of the user. The artificial intelligence engine 116 may be configured to provide, dynamically on the fly, the treatment plans and excluded treatment plans.

In some implementations, the treatment apparatus 102 may be adaptive and/or personalized because its properties, configurations, and positions may be adapted to the needs of a particular user. For example, the pedals 114 may be dynamically adjusted on the fly (e.g., via a telemedicine session or based on programmed configurations in response to certain measurements being detected) to increase or decrease a range of motion to comply with a treatment plan designed for the user. In some implementations, a healthcare professional may adapt, remotely during a telemedicine session, the treatment apparatus 102 to the needs of the user by causing a control instruction to be transmitted from the

106 server to the treatment apparatus 102. Such adaptive nature may improve the results of recovery for a user, furthering the goals of personalized medicine, and enabling personalization of the treatment plan on a per-individual basis.

Figure 10:
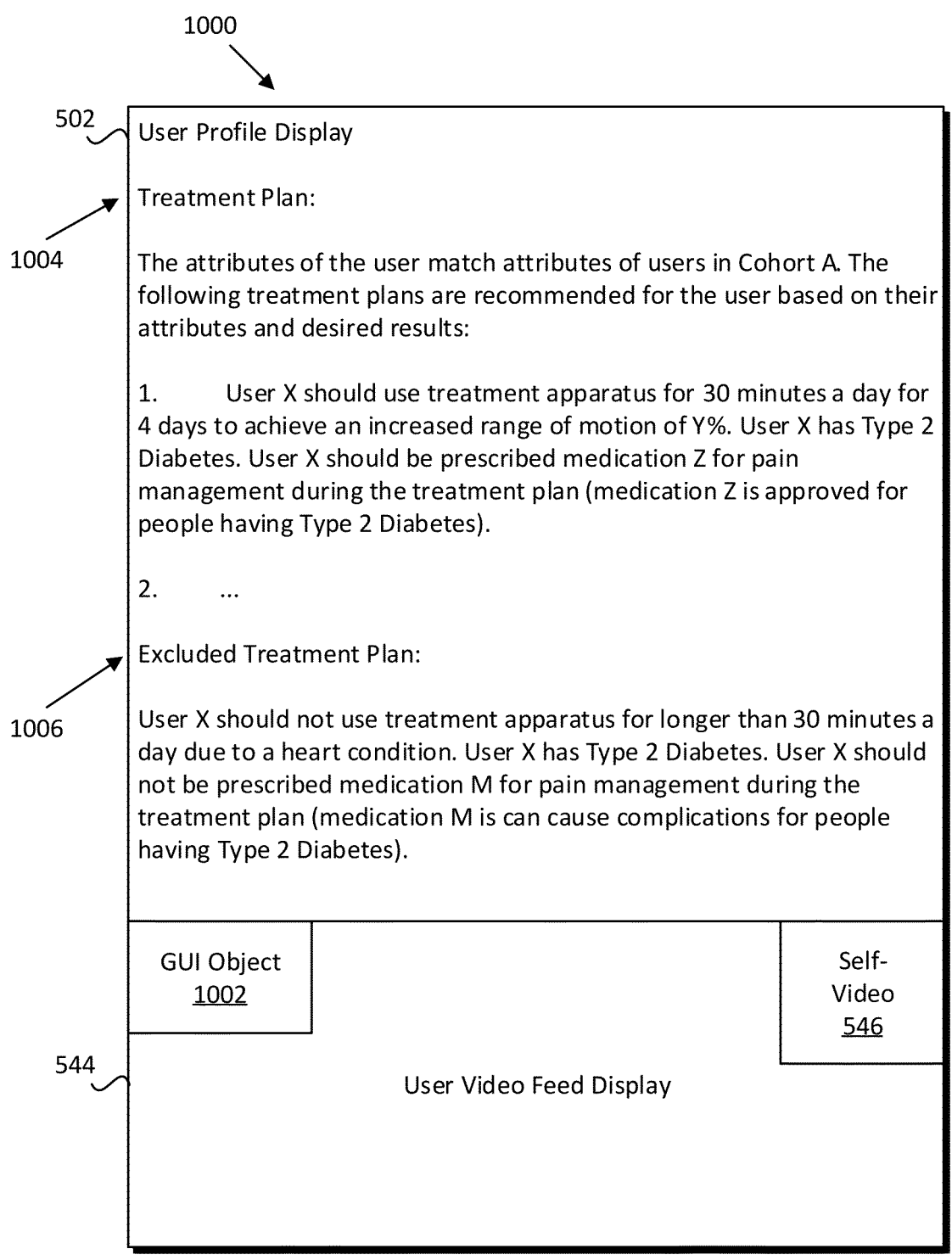
FIG. 10 is a diagram of an example of an overview display of a clinical portal presenting in real-time during a telemedicine session both recommended treatment plans and excluded treatment plans, in accordance with some implementations of the present disclosure.

FIG. 10 is a diagram of an example of an overview display 1000 of the clinical portal 124 presenting in real-time during a telemedicine session recommended treatment plans and excluded treatment plans according to the present disclosure. As depicted in FIG. 10, the overview display 1000 just includes sections for the user profile display 502 and the user video feed display 544, including the self-video display 546. Any suitable configuration of controls and interfaces of the overview display 500 described with reference to FIG. 5 may be presented in addition to or instead of the user profile display 502, the user video feed display 544, and the self-video display 546.

As further depicted in FIG. 10, the healthcare professional using the clinical portal 124 during the telemedicine session may be presented in the self-video display 546 in a portion of the overview display 1000 that also presents a video from the user in the user video feed display 544. Further, the user video feed display 544 may also include a graphical user interface (GUI) object 1002 (e.g., a button) that enables the healthcare professional to share on the user portal 122, in real-time or near real-time during the telemedicine session, the recommended treatment plans and/or the excluded treatment plans with the user. The healthcare professional may select the GUI object 1002 to share the recommended treatment plans and/or the excluded treatment plans. As depicted, another portion of the overview display 1000 includes the user profile display 502.

The user profile display 502 illustrated in FIG. 10 presents two examples of recommended treatment plans 1004 and one example of an excluded treatment plan 1006. As described herein, the treatment plans may be recommended in view of attributes of the user being treated. To generate the recommended treatment plans 1004 the user should follow to achieve a desired result, a pattern between the attributes of the user being treated and a cohort of other users who have used the treatment apparatus 102 to perform a treatment plan may be matched by one or more machine learning models 118 of the artificial intelligence engine 116. Each of the recommended treatment plans may be generated based on different desired results, i.e., different desired outcomes or best matches.

For example, as depicted in FIG. 10, the user profile display 502 presents "The attributes of the user match attributes of users in Cohort A. The following treatment plans are recommended for the user based on their attributes and desired results." Then, the user profile display 502 presents recommended treatment plans from cohort A, and each treatment plan provides different results.

As depicted in FIG. 10, treatment plan "1" indicates "User X should use treatment apparatus for 30 minutes a day for 4 days to achieve an increased range of motion of Y %. User X has Type 2 Diabetes. User X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the user to manage pain in view of a known medical disease (e.g., Type 2 Diabetes) of the user. That is, the recommended medication not only does not conflict with the medical condition of the user but thereby improves the probability of a superior user outcome. This specific example and all such examples elsewhere herein are not intended to limit in any way the generated treatment plan from recommending multiple medications, or from handling the acknowledgement, view, diagnosis and/or treatment of comorbid conditions or diseases.

As illustrated in FIG. 10, recommended treatment plan "2" may specify, based on a different desired result of the treatment plan, a different treatment plan including a different treatment protocol for a treatment apparatus, a different medication regimen, etc.

As depicted in FIG. 10, the user profile display 502 may also present the excluded treatment plan 1006. These types of treatment plans are shown to the assistant using the clinical portal 124 to alert the healthcare professional not to recommend certain portions of a treatment plan to the user. For example, the excluded treatment plan 1006 could specify the following: "User X should not use treatment apparatus for longer than 30 minutes a day due to a heart condition. User X has Type 2 Diabetes. User X should not be prescribed medication M for pain management during the treatment plan (medication M can cause complications for people having Type 2 Diabetes)." Specifically, the excluded treatment plan 1006 points out a limitation of a treatment protocol where, due to a heart condition, User X should not exercise for more than 30 minutes a day. The ruled-out treatment plan also points out that User X should not be prescribed medication M because it conflicts with the medical condition of Type 2 Diabetes.

As further depicted in FIG. 10, the healthcare professional may select the treatment plan for the user on the overview display 1000. For example, the healthcare professional may use an input peripheral (e.g., mouse, touchscreen, microphone, keyboard, etc.) to select from the treatment plans 1004 for the user. In some implementations, during the telemedicine session, the healthcare professional may discuss the pros and cons of the recommended treatment plans 1004 with the user.

In any event, the healthcare professional may select, as depicted in FIG. 10, the treatment plan for the user to follow to achieve the desired result. The selected treatment plan may be transmitted to the user portal 122 for presentation. The user may view the selected treatment plan on the user portal 122. In some implementations, the healthcare professional and the user may discuss during the telemedicine session the details (e.g., treatment protocol using treatment apparatus 102, diet regimen, medication regimen, etc.) in real-time or in near real-time. In some implementations, the server 106 may control, based on the selected treatment plan and during the telemedicine session, the treatment apparatus 102 as the user uses the treatment apparatus 102.

FIG. 11 is a diagram of an example of an overview display 1100 of the clinical portal 124 presenting, in real-time during a telemedicine session, recommended treatment plans that have changed due to user data changing according to the present disclosure. As may be appreciated, the treatment apparatus 102 and/or any computing device (e.g., user portal 122) may transmit data while the user uses the treatment apparatus 102 to perform a treatment plan. The data may include updated attributes of the user. For example, the updated attributes may include new performance information and/or measurement information related to the user, the apparatus, the environment, etc. The performance information may include a speed of a portion of the treatment apparatus 102, a range of motion achieved by the user, a force exerted on a portion of the treatment apparatus 102, a heartrate of the user, a blood pressure of the user, a respiratory rate of the user, and so forth.

In one implementation, the data received at the server 106 may be input into the trained machine learning model 118, which may determine that the attributes indicate the user is on track to achieve one or more goals associated with or part of the current treatment plan. Determining the user is on track for the current treatment plan may cause the trained machine learning model 118 to adjust a parameter of the treatment apparatus 102. The adjustment may be based on a next step of the treatment plan to further improve the performance of the user during that next step so as to more quickly achieve the one or more goals associated with or part of the current treatment plan or to surpass said one or more goals based on the adjustment.

In one implementation, the data received at the server 106 may be input into the trained machine learning model 118, which may determine that the attributes indicate the user is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 118 may determine, due to the user's not being on track or being ahead of schedule, which the attributes of the user no longer match the attributes of the users in the cohort to which the user is assigned. Accordingly, the trained machine learning model 118 may reassign the user to another cohort that includes as qualifying attributes the user's then-current attributes. As such, the trained machine learning model 118 may select a new treatment plan from the new cohort and control, based on the new treatment plan, the treatment apparatus 102. In some implementations, the trained machine learning model 118 may directly control the treatment apparatus 102 based on the new treatment plan. In other implementations, the trained machine learning model 118 may control the treatment apparatus 102 based on the new treatment plan by updating one or more programs being executed on the treatment apparatus 102 itself.

In some implementations, prior to controlling the treatment apparatus 102, the server 106 may provide the new treatment plan 1102 to the clinical portal 124 for presentation in the user profile display 502. As depicted in FIG. 11, the user profile display 502 indicates "The attributes of the user have changed and now match attributes of users in Cohort B. The following treatment plan is recommended for the user based on their attributes and desired results." Then, the user profile display 502 presents the new treatment plan 1102 ("User X should use treatment apparatus for 10 minutes a day for 3 days to achieve an increased range of motion of L %"). The healthcare professional may select the new treatment plan 1102, and the server 106 may receive the selection. The server 106 may control the treatment apparatus 102 based on the new treatment plan 1102. In some implementations, the new treatment plan 1102 may be transmitted to the user portal 122 such that the user may view the details of the new treatment plan 1102.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a user's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a user's speed of recovery, measure of quality of life, level of pain, etc. in all the foregoing procedures. In one implementation of prehabilitation, a pre-surgical procedure or a pre-non-surgical-treatment may include one or more sets of exercises for a user to perform prior to such procedure or treatment. The user may prepare an area of their body for the surgical procedure by performing the one or more sets of exercises, thereby strengthening muscle groups, improving existing and/or establishing new muscle memory, enhancing mobility, improving blood flow, and/or the like.

In some implementations, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the user, a recommended healthcare professional specialist to contact, and/or the like.

Consistent with the above disclosure, the examples of systems and methods enumerated in the following clauses are specifically contemplated and are intended as a non-limiting set of examples.

Clause 1. A method for generating, by an artificial intelligence engine, an alignment plan capable of enabling, during a treatment session, the aligning of a user's body. The method comprises: generating, by the artificial intelligence engine, one or more machine learning models trained to identify alignment plans; receiving treatment data, wherein the treatment data comprises a first position of the user's body, aspects of a treatment plan for the user, and one or more attributes of the user; generating, by the artificial intelligence engine that is configured to use the one or more machine learning models, the alignment plan, wherein the generating is based on at least the aspects of the treatment plan and at least one of the one or more attributes of the user, and wherein the alignment plan comprises a target position of the user's body and one or more elements for adjusting the user's body from the first position to the target position; and transmitting the alignment plan to a computing device.

Clause 2. The method of any clause herein, wherein the first position of the user's body is received from at least one selected from the group consisting of a camera, a RADAR sensing system, a LIDAR sensing system, an acoustic sensing system, a thermal sensing system, an ultrasonic sensing system, and a goniometer.

Clause 3. The method of any clause herein, further comprising: receiving one or more control signals at a treatment apparatus; and in response to the treatment apparatus receiving the one or more control signals, adjusting one or more portions of the treatment apparatus, wherein such adjustment complies with one or more operating parameters specified in the alignment plan.

Clause 4. The method of any clause herein, wherein the computing device comprises a clinical portal of a healthcare professional, and wherein, during a telemedicine session, the one or more control signals are transmitted in real-time or near real-time from the computing device to the treatment apparatus.

Clause 5. The method of any clause herein, further comprises presenting, to the user on a user portal associated with the computing device, one or more communications included in the one or more elements of the alignment plan, and wherein the one or more communications comprise at least one selected from the group consisting of a visual communication, a tactile communication, and an acoustic communication.

Clause 6. The method of any clause herein, wherein the user is configured to be positioned on a user support apparatus, and wherein the one or more communications comprise directions for adjusting one or more portions of the user support apparatus.

Clause 7. The method of any clause herein, wherein the one or more portions of the user support apparatus comprise at least one selected from the group consisting of a seatback, a seat rest, an armrest, a harness, a balance board, and a footrest.

Clause 8. The method of any clause herein, further comprising transmitting, in real-time or near real-time during a telemedicine session in which a clinical portal of a healthcare professional is engaged, the alignment plan to be presented on the clinical portal of the healthcare professional.

Clause 9. The method of any clause herein, further comprising generating, on a user interface, an instance of a virtual representation of the user's body, wherein the instance is enabled to characterize, in real-time or near real-time, a current position of the user's body.

Clause 10. A system for generating, by an artificial intelligence engine, an alignment plan capable of enabling, during a treatment session, the aligning of a user's body, the system comprising: a memory device for storing instructions; and a processing device communicatively coupled to the memory device, the processing device configured to execute the instructions to: generate, by the artificial intelligence engine, one or more machine learning models trained to identify alignment plans, receive treatment data, wherein the treatment data comprises a first position of the user's body, aspects of a treatment plan for the user, and one or more attributes of the user, generate, by the artificial intelligence engine that is configured to use the one or more machine learning models, the alignment plan, wherein the generating is based on at least the aspects of the treatment plan and at least one of the one or more attributes of the user, and wherein the alignment plan comprises a target position of the user's body and one or more elements for adjusting the user's body from the first position to the target position, and transmit the alignment plan to a computing device.

Clause 11. The system of any clause herein, wherein, to receive the first position of the user's body, the processing device is further configured to execute the instructions to receive the first position of the user's body from at least one selected from the group consisting of a camera, a RADAR sensing system, a LIDAR sensing system, an acoustic sensing system, a thermal sensing system, an ultrasonic sensing system, and a goniometer.

Clause 12. The system of any clause herein, further comprising a treatment apparatus configured to: receive one or more control signals, and in response to the treatment apparatus receiving the one or more control signals, adjust one or more portions of the treatment apparatus, wherein such adjustment complies with one or more operating parameters specified in the alignment plan.

Clause 13. The system of any clause herein, wherein the computing device comprises a clinical portal of a healthcare professional, and wherein, during a telemedicine session, the one or more control signals are transmitted in real-time or near real-time from the computing device to the treatment apparatus.

Clause 14. The system of any clause herein, wherein the computing device comprises a user portal of the user, wherein the user portal is configured to present, to the user, one or more communications included in the one or more elements of the alignment plan, and wherein the one or more communications comprise at least one selected from the group consisting of a visual communication, a tactile communication, and an acoustic communication.

Clause 15. The system of any clause herein, wherein the user is configured to be positioned on a user support apparatus, and wherein the one or more communications comprise directions for adjusting one or more portions of the user support apparatus.

Clause 16. The system of any clause herein, wherein the one or more portions of the user support apparatus comprise at least one selected from the group consisting of a seatback, a seat rest, an armrest, a harness, a balance board, and a footrest.

Clause 17. The system of any clause herein, wherein the processing device is further configured to execute the instructions to transmit, in real-time or near real-time during a telemedicine session in which a clinical portal of a healthcare professional is engaged, the alignment plan to be presented on the clinical portal of the healthcare professional.

Clause 18. The system of any clause herein, wherein the processing device is further configured to execute the instructions to generate, on a user interface, an instance of a virtual representation of the user's body, wherein the instance is enabled to characterize, in real-time or near real-time, a current position of the user's body.

Clause 19. A tangible, non-transitory computer-readable medium storing instructions that, when executed, cause a processing device to: generate, by an artificial intelligence engine, one or more machine learning models trained to identify alignment plans; receive treatment data, wherein the treatment data comprises a first position of a user's body, aspects of a treatment plan for the user, and one or more attributes of the user; generate, by the artificial intelligence engine that is configured to use the one or more machine learning models, an alignment plan, wherein the generating is based on at least the aspects of the treatment plan and at least one of the one or more attributes of the user, and wherein the alignment plan comprises a target positions of the user's body and one or more elements for adjusting the user's body from the first position to the target position; and transmit the alignment plan to a computing device.

Clause 20. The computer-readable medium of any clause herein, wherein, to receive the first position of the user's body, the processing device is further configured to execute the instructions to receive the first position of the user's body from at least one selected from the group consisting of a camera, a RADAR sensing system, a LIDAR sensing system, an acoustic sensing system, a thermal sensing system, an ultrasonic sensing system, and a goniometer.

Clause 21. The computer-readable medium of any clause herein, further comprising a treatment apparatus configured to: receive one or more control signals, and in response to the treatment apparatus receiving the one or more control signals, adjust one or more portions of the treatment apparatus, wherein such adjustment complies with one or more operating parameters specified in the one or more alignment plan.

Clause 22. The computer-readable medium of any clause herein, wherein the computing device comprises a clinical portal of a healthcare professional, and wherein, during a telemedicine session, the one or more control signals are transmitted in real-time or near real-time from the computing device to the treatment apparatus.

Clause 23. The computer-readable medium of any clause herein, wherein the computing device comprises a user portal of the user, wherein the user portal is configured to present, to the user, one or more communications included in the one or more elements of the alignment plan, and wherein the one or more communications comprise at least one selected from the group consisting of a visual communication, a tactile communication, and an acoustic communication.

Clause 24. The computer-readable medium of any clause herein, wherein the user is configured to be positioned on a user support apparatus, and wherein the one or more communications comprise directions for adjusting one or more portions of the user support apparatus.

Clause 25. The computer-readable medium of any clause herein, wherein the one or more portions of the user support apparatus comprise at least one selected from the group consisting of a seatback, a seat rest, an armrest, a harness, a balance board, and a footrest.

Clause 26. The computer-readable medium of any clause herein, wherein the processing device is further configured to execute the instructions to transmit, in real-time or near real-time during a telemedicine session in which a clinical portal of a healthcare professional is engaged, the alignment plan to be presented on the clinical portal of the healthcare professional.

Clause 27. The computer-readable medium of any clause herein, wherein the processing device is further configured to execute the instructions to generate, on a user interface, an instance of a virtual representation of the user's body, wherein the instance is enabled to characterize, in real-time or near real-time, a current position of the user's body.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A method for generating, by an artificial intelligence engine, an alignment plan capable of enabling, during a treatment session, the aligning of a user's body, the method comprising:

generating, by the artificial intelligence engine, one or more machine learning models trained to identify alignment plans;

receiving treatment data, wherein the treatment data comprises a first position of the user's body while the user is engaged with a treatment apparatus, aspects of a treatment plan for the user, and one or more attributes of the user, wherein the treatment apparatus includes at least one pedal;

receiving cohort user data comprising one or more attributes of respective users associated with the cohort user data, and alignment plan data associated with alignment plans performed by the respective users associated with the cohort user data, wherein at least some of the one or more attributes of the respective users associated with the cohort user data correspond to at least some of the one or more attributes of the user in the treatment data;

generating, by the artificial intelligence engine that is configured to use the one or more machine learning models, the alignment plan, wherein the generating is based on at least the aspects of the treatment plan, at least some of the cohort user data; and at least one of the one or more attributes of the user, and wherein the alignment plan comprises a target position of the user's body and one or more elements for adjusting the user's body from the first position to the target position;

transmitting the alignment plan to a computing device;

receiving output from the computing device, wherein the output is generated by the computing device and based on at least the alignment plan; and adjusting, based on the output from the computing device, at least one aspect of the treatment apparatus.

2. The method of claim 1, wherein the first position of the user's body is received from at least one selected from the group consisting of a camera, a RADAR sensing system, a LIDAR sensing system, an acoustic sensing system, a thermal sensing system, an ultrasonic sensing system, and a goniometer.

3. The method of claim 1, wherein adjusting the at least one aspect of the treatment apparatus complies with one or more operating parameters specified in the alignment plan.

4. The method of claim 3, wherein the computing device comprises a clinical portal of a healthcare professional, and wherein, during a telemedicine session, the one or more control signals are transmitted in real-time or near real-time from the computing device to the treatment apparatus.

5. The method of claim 1, further comprises presenting, to the user on a user portal associated with the computing device, one or more communications included in the one or more elements of the alignment plan, and wherein the one or more communications comprise at least one selected from the group consisting of a visual communication, a tactile communication, and an acoustic communication.

6. The method of claim 5, wherein the user is configured to be positioned on a user support apparatus, and wherein the one or more communications comprise directions for adjusting one or more portions of the user support apparatus.

7. The method of claim 6, wherein the one or more portions of the user support apparatus comprise at least one selected from the group consisting of a seatback, a seat rest, an armrest, a harness, a balance board, and a footrest.

8. The method of claim 5, further comprising transmitting, in real-time or near real-time during a telemedicine session in which a clinical portal of a healthcare professional is engaged, the alignment plan to be presented on the clinical portal of the healthcare professional.

9. The method of claim 1, further comprising generating, on a user interface, an instance of a virtual representation of the user's body, wherein the instance is enabled to characterize, in real-time or near real-time, a current position of the user's body.

10. A system for generating, by an artificial intelligence engine, an alignment plan capable of enabling, during a treatment session, the aligning of a user's body, the system comprising:

a memory device for storing instructions; and a processing device communicatively coupled to the memory device, the processing device configured to execute the instructions to:

generate, by the artificial intelligence engine, one or more machine learning models trained to identify alignment plans;

receive treatment data, wherein the treatment data comprises a first position of the user's body while the user is engaged with a treatment apparatus, aspects of a treatment plan for the user, and one or more attributes of the user, wherein the treatment apparatus includes at least one pedal;

receive cohort user data comprising one or more attributes of respective users associated with the cohort user data, and alignment plan data associated with alignment plans performed by the respective users associated with the cohort user data, wherein at least some of the one or more attributes of the respective users associated with the cohort user data correspond to at least some of the one or more attributes of the user in the treatment data;

generate, by the artificial intelligence engine that is configured to use the one or more machine learning models, the alignment plan, wherein the generating is based on at least the aspects of the treatment plan, at least some of the cohort user data, and at least one of the one or more attributes of the user, and wherein the alignment plan comprises a target position of the user's body and one or more elements for adjusting the user's body from the first position to the target position;

transmit the alignment plan to a computing device;

receive output from the computing device, wherein the output is generated by the computing device and based on at least the alignment plan; and adjust, based on the output from the computing device, at least one aspect of the treatment apparatus.

11. The system of claim 10, wherein, to receive the first position of the user's body, the processing device is further configured to execute the instructions to receive the first position of the user's body from at least one selected from the group consisting of a camera, a RADAR sensing system, a LIDAR sensing system, an acoustic sensing system, a thermal sensing system, an ultrasonic sensing system, and a goniometer.

12. The system of claim 10, wherein adjusting the at least one aspect of the treatment apparatus complies with one or more operating parameters specified in the alignment plan.

13. The system of claim 12, wherein the computing device comprises a clinical portal of a healthcare professional, and wherein, during a telemedicine session, the one or more control signals are transmitted in real-time or near real-time from the computing device to the treatment apparatus.

14. The system of claim 10, wherein the computing device comprises a user portal of the user, wherein the user portal is configured to present, to the user, one or more communications included in the one or more elements of the alignment plan, and wherein the one or more communications comprise at least one selected from the group consisting of a visual communication, a tactile communication, and an acoustic communication.

15. The system of claim 14, wherein the user is configured to be positioned on a user support apparatus, and wherein the one or more communications comprise directions for adjusting one or more portions of the user support apparatus.

16. The system of claim 15, wherein the one or more portions of the user support apparatus comprise at least one selected from the group consisting of a seatback, a seat rest, an armrest, a harness, a balance board, and a footrest.

17. The system of claim 14, wherein the processing device is further configured to execute the instructions to transmit, in real-time ore near real time during a telemedicine session in which a clinical portal of a healthcare professional is engaged, the alignment plan to be presented on the clinical portal of the healthcare professional.

18. The system of claim 10, wherein the processing device is further configured to execute the instructions to generate, on a user interface, an instance of a virtual representation of the user's body, wherein the instance is enabled to characterize, in real-time or near real-time, a current position of the user's body.

19. A tangible, non-transitory computer-readable medium storing instructions that, when executed, cause a processing device to:

generate, by an artificial intelligence engine, one or more machine learning models trained to identify alignment plans;

receive treatment data, wherein the treatment data comprises a first position of a user's body while the user is engaged with a treatment apparatus, aspects of a treatment plan for the user, and one or more attributes of the user, wherein the treatment apparatus includes at least one pedal;

receive cohort user data comprising one or more attributes of respective users associated with the cohort user data, and alignment plan data associated with alignment plans performed by the respective users associated with the cohort user data, wherein at least some of the one or more attributes of the respective users associated with the cohort user data corresponds to at least some of the one or more attributes of the user in the treatment data;

generate, by the artificial intelligence engine that is configured to user the one or more machine learning models, an alignment plan, wherein the generating is based on at least the aspects of the treatment plan, at least some of the cohort user data, and at least one of the one or more attributes of the user, and wherein the alignment plan comprises a target position of the user's body and one or more elements for adjusting the user's body from the first position to the target position;

transmit the alignment plan to a computing device;

receive output from the computing device, wherein the output is generated by the computing device and based on at least the alignment plan; and adjust, based on the output from the computing device, at least one aspect of the treatment apparatus.

20. The computer-readable medium of claim 19, wherein, to receive the first position of the user's body, the processing device is further configured to execute the instructions to receive the first position of the user's body from at least one selected from the group consisting of a camera, a RADAR sensing system, a LIDAR sensing system, an acoustic sensing system, a thermal sensing system, an ultrasonic sensing system, and a goniometer.

* * * * *